(12) United States Patent
Tan Hehir et al.

(10) Patent No.: US 8,617,515 B2
(45) Date of Patent: Dec. 31, 2013

(54) IMAGING OF MYELIN BASIC PROTEIN

(75) Inventors: Cristina Abucay Tan Hehir, Niskayuna, NY (US); Tiberiu Mircea Siclovan, Rexford, NY (US); Nicole Evelyn Barnhardt, Clifton Park, NY (US); Kenneth Michael Fish, Clifton Park, NY (US); Randall Lee Carter, Clifton Park, NY (US); Bruce Fletcher Johnson, Scotia, NY (US)

(73) Assignee: General Electric Company, Niskayuna, NY (US)

( * ) Notice: Subject to any disclaimer, the term of this patent is extended or adjusted under 35 U.S.C. 154(b) by 658 days.

(21) Appl. No.: 12/478,300

(22) Filed: Jun. 4, 2009

(65) Prior Publication Data

US 2010/0310457 A1 Dec. 9, 2010

(51) Int. Cl.
| | |
|---|---|
| *A61K 49/00* | (2006.01) |
| *A61K 49/10* | (2006.01) |
| *A61K 51/04* | (2006.01) |
| *A61K 101/02* | (2006.01) |
| *A61B 5/00* | (2006.01) |
| *A61B 5/055* | (2006.01) |

(52) U.S. Cl.
USPC ......... 424/1.65; 424/1.81; 424/1.89; 424/9.1; 424/9.3; 424/9.37; 424/9.6; 600/420

(58) Field of Classification Search
None
See application file for complete search history.

(56) References Cited

U.S. PATENT DOCUMENTS

| | | |
|---|---|---|
| 6,229,024 B1 | 5/2001 | Schmued |
| 6,372,451 B1 | 4/2002 | Schmued |
| 2003/0232016 A1 | 12/2003 | Helnrich |
| 2007/0028032 A1 | 2/2007 | Baba |

FOREIGN PATENT DOCUMENTS

WO    WO2009029936    3/2009

OTHER PUBLICATIONS

Stankoff B, Wang Y, Bottlaender M, Aigrot MS, Dolle F, Wu C, Feinstein D, Huang GF, Semah F, Mathis CA, Klunk W, Gould RM, Lubetzki C, Zalc B. Imaging of CNS myelin by positron-emission tomography. 2006 Proc. Natl. Acad. Sci. USA 103: 9304-9309 and supporting information p. 1-3.*
Detert H, Sugiono E. Soluble oligo(phenylenevinylene)s with electron withdrawing substituents for the use in light emitting diodes. 2000 Synth. Met. 115: 89-92.*
Monici M. Cell and tissue autofluorescence research and diagnostic applications. 2005 Biotechnol. Annu. Rev. 11: abstract only.*
Kung MP, Hou C, Zhuang ZP, Skovronsky DM, Zhang B, Gur TL, Trojanowski JQ, Lee VM, Kung HF. Radioiodinated styrylbenzene derivatives as potential SPECT imaging agents for amyloid plaque detection in Alzheimer's disease. 2002 J. Mol. Neurosci. 19: 7-10.*
Higuchi M, Iwata N, Matsuba Y, Sato K, Sasamoto K, Saido TC. 19F and 1H MRI detection of amyloid beta plaques in vivo. 2005 Nat. Neurosci. 8: 527-533.*
Sun YH, Zhao K, Wang CK, Luo Y, Ren Y, Tao XT, Jiang MH. Two-photon absorption properties of multi-branched bis-(styryl)benzene based organic chromophores. 2004 J. Mol. Struct. (Theochem) 682: 185-189.*
Wu et al. "A Novel Fluorescent Prpbe That is Brain Permeable and Selectively Binds to Myelin", Journal of Histochemistry and Cytochemistry, vol. 54, 2006, pp. 1-9.
Fridkis-Harelli et al., "Direct Binding of Myelin Basic Protein and Synthetic Copolymer I to Class II Major Histocompatibility Complex Molecules on Living Antigen-Presenting Cells—Specificity and Promiscuity", Proc. Natl. Acad. Sci., vol. 91, pp. 4872-4876, May 1994.
"Tracers for Membrane Labeling—Section 14.4", Molecular Probes, pp. 1-10 , 2009.
U.S. Appl. No. 12/211,254, filed Sep. 17, 2008.
U.S. Appl. No. 12/370,207, filed Feb. 12, 2009.
Wu et al., "Molecular Probes for Imaging Myelinated White Matter in CNS", Journal of Medicinal Chemistry, 2008, 51 (21), pp. 6682-6688.
Xiang et al., "Detection of Myelination Using a Novel Histological Probe", J. Histochem. Cytochem., 2005, 53(12) , pp. 1511-1516.
Unofficial English translation of Office Action from CN dated Aug. 1, 2013.

* cited by examiner

*Primary Examiner* — Michael G Hartley
*Assistant Examiner* — Jennifer Lamberski
(74) *Attorney, Agent, or Firm* — Eileen W. Gallagher

(57) ABSTRACT

The present invention relates to methods for myelin basic protein detection comprises identifying a subject at risk of or diagnosed with a myelin-associated neuropathy, parenterally administering to the subject the agent, and determining myelination in the subject by detecting binding to myelin basic protein. Methods for the detection of myelin and a quantitative measurement of its local concentration in a sample using an agent with specific binding to myelin basic protein are also provided as is a kit containing the agent or its derivatives for use in detecting myelin basic protein.

28 Claims, 6 Drawing Sheets

Formula Ia
$R^1=CH_3, R^2=NH_2, R^3=CN$

IMAGING OF MYELIN BASIC PROTEIN

BACKGROUND

Information flow within the nervous system requires the perpetuation of ionic gradients along neurons. In many neurons, effective and efficient perpetuation of such gradients along axons requires electrical insulation. Myelin, a lipid-rich, dielectric substance that ensheathes axons, serves this insulating function. The nervous system contains high levels of myelin, which is especially enriched where many myelinated axons are bundled together, such as in tracts of the spinal cord and spinal nerve roots, nerves in the peripheral nervous system, and fiber tracts in the brain, collectively called "white matter", as opposed to "grey matter". Because non-nervous system tissue lacks myelin, the presence of myelin can distinguish nerve tissue from other tissue types; the spinal cord and spinal nerve roots from non-nervous elements of the vertebral column, and white matter from grey matter in the brain.

The ability to qualitatively or quantitatively visualize myelin, either in vivo or in vitro, confers upon researchers and clinicians important diagnostic and treatment tools. For example, the ability to visually identify peripheral nerves during surgery assists surgeons in avoiding cutting or damaging nerves. Previous efforts in image-guided surgery of nerves utilized modalities that would not require contrast agents or fluorescent labeling of axons by retrograde transport. A challenge in the first approach is that the signal is typically ambiguous Retrograde labeling of nerves in animal models is widely reported in the literature. Although this strategy may work, there are many inherent problems. Labeling would depend on exactly where the contrast agent is injected. If the nerves fail to take up the contrast agent, the nerve would not be visualized. In some cases, nerve stimulation is required to facilitate retrograde transport. The long times required for retrograde transport may not be clinically feasible.

Myelinated nerves and fiber tracts serve as useful landmarks in anatomical studies carried out by preclinical and basic neuroscience researchers. Furthermore, the formation of myelin sheaths is an important step in the generation and functional stability of new neurons; so the availability of myelin markers may aid researchers study such processes. Myelin-labeling methodologies are also useful in the development of numerous therapies, neural stem cell research, and putative animal models of myelin-associated neuropathies. In vivo myelin imaging of the spinal cord assists clinicians in the diagnosis and treatment of spinal cord pathology, such as nerve compression or herniated discs as well as myelin-associated neuropathies, such as multiple sclerosis which results in damage to myelin within the central or peripheral nervous system. The ability to measure amounts of myelination in vivo in patients with such conditions would aid clinicians and researchers in diagnosing and prognosing myelin-associated neuropathies.

The spinal nerve roots can be damaged as they traverse the spinal canal, but are especially vulnerable in the intervertebral foramen, where the spinal nerve roots join to form the spinal nerves. Syndromes such as cervical radiculopathy, sciatica, intervertebral disc herniation, and root compression are caused by compression primarily from tumors or other lesions, which usually present with back or neck pain. Back or neck pain may be caused by a variety of musculoskeletal mechanisms and the physician needs to be able to examine the nervous system to determine if there is compression of nerve roots or the spinal cord. The ability to image and identify the source of chronic neck or back pain could enable surgeons to effectively treat these syndromes.

Myelin-labeling methodologies do exist, including the use of commercially available FluoroMyelin dyes for identification of high myelin content tissues. However, except for a few dyes such as bis-styrene-arylene dyes such as 1,4-bis(p-aminostyryl)-2-methoxy benzene (BMB), and (E,E)-1,4-bis(4'-aminostyryl)-2-dimethoxy-benzene (BDB), most of the publicly-disclosed dyes are unable to cross the blood nerve or blood brain barrier.

Myelin is a protein and lipid-rich matrix formed by oligodendrocytes in the central nervous system (CNS) and Schwann cells in the peripheral nervous system (PNS). Because two different cell types in CNS and PNS produce myelin, namely oligodendrocytes and Schwann cells respectively, there are similarities and differences in protein and lipid composition depending on the source of myelin. In both instances, myelin is composed of about 80% lipid fraction and about 20% protein fraction. Numerous studies have examined the molecular components of both fractions.

The lipid fraction in myelin contain cholesterol, cholesterol ester, cerebroside, sulfatide, sphingomyelin, phosphotidylethanolomine, phosphotidylcholine, phosphotidylserine, phosphotidylinositol, triacylglycerol, and diacylglycerol. The protein fraction is composed of several proteins, which include myelin basic protein (MBP), peripheral myelin protein 22 (PMP22), connexin 32 and myelin-associated glycoprotein (MAG), which are, produced by both PNS and CNS cells; the protein myelin protein zero (MPZ), produced by the PNS only; and proteolipid protein, produced by CNS cells only.

MBP is a major protein component of myelin at 5%-15%, which translates into about 5 mM concentration of MBP. Techniques such as circular dichroism, NMR and EPR spectroscopy, atomic force microscopy and others, suggest that MBP may have a compact C-shaped form with a core element of beta-sheet structure, but only when associated with lipids. The interaction of myelin basic protein to lipids can cause conformational variability and may be critical for function.

An agent that selectively binds to MBP may result in improvements in myelin staining and thereby aid in nerve visualization. Nerve visualization my be further improved through, optimal elimination of unbound and nonspecifically bound dye, and improved optical properties to allow enhanced contrast between myelin and surrounding tissue. Optical properties in the near infrared range (NIR), between 700-900 nm, are ideal for visualization of myelin in vivo. In the NIR range the absorption of water, hemoglobin, and lipid are minimal, and scatter is reduced such that photon penetration is improved. Also, autofluorescence is low and the NIR light penetrates deep into tissue and is less affected by scatter.

BRIEF DESCRIPTION

Provided herein are methods for the detection of myelin-associated neuropathy comprising identifying a subject at risk of or diagnosed with a myelin-associated neuropathy, administering to a subject an agent that binds specifically to myelin basic protein, and determining myelination in the subject by detecting the agent present in the subject.

In one embodiment the agent comprises a compound of Formula I, a $^{13}$C enriched compound of Formula I, an 19F-labeled derivative of Formula I, or a radioisotope derivative of Formula I

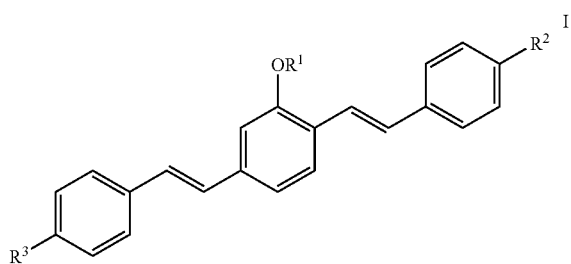

wherein $R^1$ is an alkyl group, $R^2$ is an electron donating group and $R^3$ is an electron withdrawing group; or $R^2$ is an electron withdrawing group and $R^3$ is an electron donating group.

In another embodiment a kit for detecting myelin-associated neuropathy in a subject is provided, the kit comprising an agent at binds specifically to myelin basic protein and a pharmaceutically acceptable carrier.

BRIEF DESCRIPTION OF THE FIGURES

These and other features, aspects, and advantages of the present invention will become better understood when the following detailed description is read with reference to the accompanying figures wherein.

DETAILED DESCRIPTION

Figure 1A:
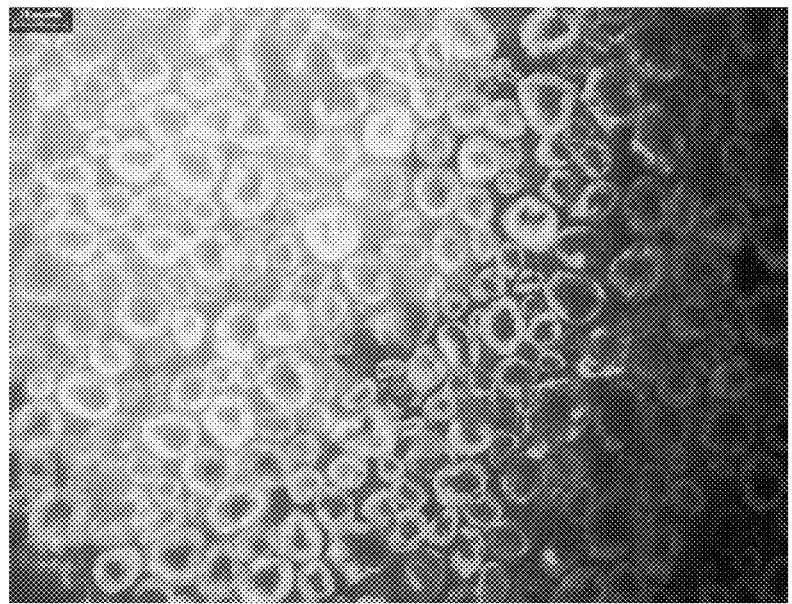
FIG. 1 shows results from fluorescence microscopy examination of a trigeminal nerve tissue section of a rat stained with myelin basic protein (MBP) antibody (FIG. 1A) and BMB (FIG. 1B). The magnification is 1000×.

The following detailed description is exemplary and not intended to limit the invention of the application and uses of the invention. Furthermore, there is no intention to be limited by any theory presented in the preceding background of the invention or descriptions of the drawings.

DEFINITIONS

To more clearly and concisely describe and point out the subject matter of the claimed invention, the following definitions are provided for specific terms, which are used in the following description and the appended claims.

"Myelin-associated neuropathy" generally refers to any condition in which the insulating material ensheathing portions of neuronal cells becomes damaged or dysfunctional as a component of a syndrome, disease, or other pathological condition, such as, but not limited to, multiple sclerosis, Guillain-Barré syndrome, leukodystrophies, metachromatic leukodystrophy, Refsum's disease, adrenoleukodystrophy, Krabbe's disease, phenylketonuria, Canavan disease, Pelizaeus-Merzbacher disease, Alexander's disease, diabetic neuropathy, chemotherapy induced neuropathy, or any combination thereof.

"Agent" refers to a solution or carrier for introducing a compound into a subject in a manner to allow the compound to be administered at a desired concentration and efficacy. The agent may include, but is not limited to, solvents, stabilization aids, buffers, and fillers.

An agent exhibits "specific binding" for myelin if it associates more frequently with, more rapidly with, for a longer duration with, or with greater affinity to, myelin than with tissues not containing myelin. "Non-specific binding" refers to binding of the agent to non-myelin containing tissue. For relative binding values, such as specific binding or non-specific binding, each sample should be measured under similar physical conditions (i.e., temperature, pH, formulation, and mode of administration). Generally, specific binding is characterized by a relatively high affinity of an agent to a target and a relatively low to moderate capacity. Typically, binding is considered specific when the affinity constant $K_a$ is at least $10^6 \text{ M}^{-1}$. A higher affinity constant indicates greater affinity, and thus typically greater specificity. For example, antibodies typically bind antigens with an affinity constant in the range of $10^6 \text{ M}^{-1}$ to $10^9 \text{ M}^{-1}$ or higher. "Non-specific" binding usually has a low affinity with a moderate to high capacity. Non-specific binding usually occurs when the affinity constant is below $10^6 \text{ M}^{-1}$. Controlling the time and method used to contact the agent with the tissues reduces non-specific binding.

"Washing" generally refers to any method, such as but not limited to, immersion in, or flushing by repeated application of, a non-labeling solution or other substance, such as but not limited to water, saline, buffered saline, or ethanol, so as to provide a medium for dissociation, dispersal, and removal of unbound or non-specifically bound labeling compound from non-myelinated components of the tissue or sample of tissue without eliminating specific binding to myelin.

"Baseline fluorescence" refers to the frequency and magnitude of electromagnetic radiation emitted by a tissue or sample of tissue upon being exposed to an external source of electromagnetic radiation in the absence of administration or binding of any fluorescing compound, as distinguished from the radiation emitted following the administration and binding of such fluorescing compound and exposure to an external source of electromagnetic radiation.

"Control sample representative of the tissue section" refers to a tissue sample of a similar size, morphology, or structure as the tissue sample to be analyzed, and with a level of myelin whereby the sample's level of myelin serves as a reference to which other samples' myelin levels may be compared.

"Parenteral administration" refers to any means of introducing a substance or compound into a subject, that does not involve oral ingestion or direct introduction to the gastrointestinal tract, including but not limited to subcutaneous injection, intraperitoneal injection, intramuscular injection, intravenous injection, intrathecal injection, intracerebral injection, intracerebroventricular injection, intraspinal injection, intrathecal injection, intracerebral injection, intracerebroventricular injection, or intraspinal injection or any combination thereof.

"Pharmaceutical carrier" refers to a composition which allows the application of the agent material to the site of the application, surrounding tissues, or prepared tissue section to allow the agent to have an effective residence time for specific binding to the target or to provide a convenient manner of release. Solubilization strategies may include but are not limited to: pH adjustments, salt formation, formation of ionizable compounds, use of co-solvents, complexation, surfactants and micelles, emulsions and micro-emulsions. The pharmaceutical carrier may include, but is not limited to, a solubilizer, detergent, buffer solution, stabilizers, and preservatives. Examples of these include but are not limited to, HCl, citric acid, DMSO, propylene glycol, ethanol PEG 300, cyclodextrans, citrate, acetate, phosphate, carbonate or tris (hydroxymethyl)aminomethane.

"Demyelination model" refers to any experimentally-induced damage to, or dysfunction of, the insulating material ensheathing portions of neuronal cells, that may be utilized in the experimental study of neuropathic demyelination, including, but not limited to, experimental allergic encephalomyelitis.

"Remyelination" refers to the spontaneous, therapeutic, or experimentally induced repair, regeneration, or otherwise enhanced constitution or functionality of the insulating material ensheathing neuronal axons.

"Alkyl" is intended to include linear, branched, or cyclic hydrocarbon structures and combinations thereof, including lower alkyl and higher alkyl. Alkyl groups are those of C20 or below. "Lower alkyl" refers to alkyl groups of from 1 to 6 carbon atoms, preferably from 1 to 4 carbon atoms, and includes methyl, ethyl, n-propyl, isopropyl, and n-, s- and t-butyl. Higher alkyl refers to alkyl groups having seven or more carbon atoms, preferably 7-20 carbon atoms, and includes n-, s- and t-heptyl, octyl, and dodecyl. Cycloalkyl is a subset of alkyl and includes cyclic hydrocarbon groups of from 3 to 8 carbon atoms. Examples of cycloalkyl groups include cyclopropyl, cyclobutyl, cyclopentyl, and norbornyl. Alkenyl and alkynyl refer to alkyl groups wherein two or more hydrogen atoms are replaced by a double or triple bond, respectively.

"Substituted" refers to residues, including, but not limited to, alkyl, alkylaryl, aryl, arylalkyl, and heteroaryl, wherein up to three H atoms of the residue are replaced with lower alkyl, substituted alkyl, aryl, substituted aryl, haloalkyl, alkoxy, carbonyl, carboxy, carboxalkoxy, carboxamido, acyloxy, amidino, nitro, halo, hydroxy, OCH(COOH)$_2$, cyano, primary amino, secondary amino, acylamino, alkylthio, sulfoxide, sulfone, phenyl, benzyl, phenoxy, benzyloxy, heteroaryl, or heteroaryloxy.

"Electron donating group" refers to chemical groups that add electron density to the conjugated π system making it more nucleophilic. Electron donating groups may be recognized by lone pairs of electrons on an atom adjacent to the π system. Examples of electron donating groups include, but are not limited to, —NR'R", —NHR, —NH$_2$, —OH, —OR, —NHCOR, —OCOR, —R, —C$_6$H$_5$, and —CH=CR$_2$.

"Electron withdrawing group" refers to chemical groups that remove electron density from the conjugated π system rendering the structure less nucleophilic. Electron withdrawing groups may be recognized either by the atom adjacent to the π system having several bonds to more electronegative atoms or, having a formal positive charge. Examples of electron withdrawing groups include, but are not limited to, —COH, —COR, —COOR, —COOH, —COCl, —CF$_3$, —CN, C=C(CN)$_2$—SO$_3$H, —NH$_3$+, —NR$_3$+, —NO$_2$ An agent exhibits "specific uptake" for myelinated tissues if it associates more frequently with, more rapidly with, for a longer duration with, or with greater affinity to, or if it is absorbed more, or accumulates more in myelinated tissues than with non-myelinated tissues. Generally, specific uptake is characterized by a relatively high affinity of an agent to a target.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Many of the compounds described herein may comprise one or more asymmetric centers and may thus give rise to enantiomers, diastereomers, and other stereoisomeric forms that may be defined, in terms of absolute stereochemistry, as (R)— or (S)—. The chemical structure of the agent includes for example, without limitation, all such possible isomers, as well as, their racemic and optically pure forms. Optically active (R)— and (S)— isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also included.

In certain embodiments, methods for the qualitative or quantitative detection of myelin basic protein in an in vitro or in vivo sample utilizing specific binding of an agent to myelin basic protein is provided. The specific binding to myelin basic protein may be by an agent comprising the compound of Formula I, a $^{13}$C enriched compound of Formula I, an $^{19}$F-labeled-derivative of Formula I, or a radioisotope derivative of Formula I,

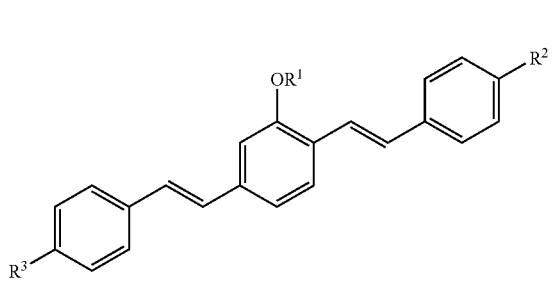

wherein R$^1$ is an alkyl group, R$^2$ is an electron donating group and R$^3$ is an electron withdrawing group, or R$^2$ is an electron withdrawing group and R$^3$ is an electron donating group.

In certain embodiments R$^1$ may be a lower alkyl groups of from 1 to 6 carbon atoms, preferably from 1 to 4 carbon atoms, and includes methyl, ethyl, n-propyl, isopropyl, and n-, s- and t-butyl. The electron donating group may include a primary, secondary, or tertiary amine (—NH2, NHR, NR'R"), or an alkoxy group (—OR). R3 may include a nitrile group (—CN) or an ester (—COOR).

In each embodiment, R$^2$ and R$^3$ are conjugated through the π double bond orbitals of the benzene rings and olefinic substituents, thereby providing a clear path for electrons to flow from the electron donating group to the electron withdrawing group. The electron-donating group may be in the $R^2$ or $R^3$ position provided that an electron-withdrawing group is in the alternative position.

This conjugation and "push-pull" electron flow from $R^2$ to $R^3$ may be responsible for a Stokes shift of a longer wavelength during fluorecence as compared to BMB and BDB. In applications, this may allow enhanced contrast between myelin and surrounding tissue when using an agent of Formula I.

In some embodiments, the agent, which specifically binds to myelin basic protein, may be a radioisotope, a $^{13}C$ enriched compound, or an $^{19}F$-labeled derivative. In some embodiments, a radioisotope derivative of the compound of Formula I may be prepared and imaging accomplished through radioimaging. Alternatively, a $^{13}C$ enriched compound of Formula I, or an $^{19}F$-labeled derivative of Formula I may be prepared.

The agent comprising the compound of Formula I, a $^{13}C$ enriched compound of Formula I, an $^{19}F$-labeled-derivative of Formula I, or a radioisotope derivative of Formula I, may be detected by its emitted signal, such as a magnetic resonance signal or emitted radiation from a radioisotope derivative of Formula I, autofluorescence emission, or optical properties of the agent. The method of detection of agent comprising the compound of Formula I, a $^{13}C$ enriched compound of Formula I, an $^{19}F$-labeled-derivative of Formula I, or a radioisotope derivative of Formula I, may include fluorescence microscopy, laser-confocal microscopy, cross-polarization microscopy, nuclear scintigraphy, positron emission tomography ("PET"), single photon emission computed tomography ("SPECT"), magnetic resonance imaging ("MRI"), magnetic resonance spectroscopy ("MRS"), computed tomography ("CT"), or a combination thereof, depending on the intended use and the imaging methodology available to the medical or research personnel.

The imaging methods described may be applicable to analytical, diagnostic, or prognostic applications related to myelin basic protein detection. The applications may be particularly applicable in intraoperative nerve labeling, spinal imaging, brain tissue imaging, non-invasive in vivo measurement of myelination levels, and preclinical and basic neuroscience bench research aimed at the study of the function and process of myelination, and the dysfunction and repair of myelin.

In one embodiment, an agent which binds specifically to myelin basic protein may be administered parenterally to a surgical subject prior to surgery such that the agent binds to myelin basic protein and may be cleared from tissues that do not contain myelin basic protein. In another embodiment, the agent may be applied directly, via painting on, spraying on, or local injection to the surgical field during surgery, allowed to bind to myelin basic protein present, and the surgical site washed by lavage to clear unbound composition from the site. During surgery, a light source tuned to the spectral excitation characteristics of the agent may be applied to the surgical field. The agent may be observed through an optical filter tuned to its spectral emission characteristics. Due to their specific binding to the fluorescing agent, nerves and other myelin containing tissue are distinguishable from tissue not containing myelin basic protein. This enables the surgeon to avoid inadvertently cutting or damaging myelinated tissue by avoiding fluorescing tissue, or facilitates accurately administering treatment to the intended myelinated tissue. In certain embodiments the agent comprises the compound of Formula I.

An agent which specifically binds to myelin basic protein may be administered parenterally to a subject prior to surgery or prior to treatments targeting a nerve or other myelin containing tissue, such as pharmaceutical or surgical nerve block. In certain embodiments the myelinated tissue may be part of the spinal canal and intervertebral foramen. In other embodiments the myelinated tissue may be part of the brain. In certain embodiments the agent comprises the compound of Formula I, a $^{13}C$ enriched compound of Formula I, an $^{19}F$-labeled-derivative of Formula I, or a radioisotope derivative of Formula I In one embodiment an agent, such as one comprising the compound of Formula I, a $^{13}C$ enriched compound of Formula I, or an $^{19}F$-labeled-derivative of Formula I, may be administered parenterally to a surgical subject, prior to surgery, to permit binding to myelin basic protein, and clearance from tissues that do not contain myelin basic protein without the elimination of specific myelin basic protein binding.

In another embodiment, an agent which is a radioisotope and which specifically binds to myelin basic protein may be administered parenterally to a subject prior to treatment to allow binding and clearance from tissues that do not contain myelin. Imaging techniques such as nuclear scintigraphy, PET, SPECT, CT, MRI, MRS, or any combination thereof, may then be used to aid in differentiation of the myelin and non-myelin containing tissues and may employ a gamma camera, a scanner or a probe. The agent may be a radioisotope derivative of the compound of Formula I In another embodiment an agent, such as one comprising the compound of a radioisotope derivative of Formula I, may be administered parenterally to a patient suspected of, or determined to be, suffering from a spinal pathology, such as but not limited to, spinal compression, spinal nerve root compression, or a bulging disc. After binding to spinal myelin basic protein, and clearance from tissue that does not contain myelin basic protein without eliminating the specific myelin basic protein binding, the spine may be imaged for in vivo using radioisotope imaging such as PET, SPECT, or any combination thereof.

By inspection of the diagnostic images, the clinician may determine if, and where, the spinal cord, or associated nerve roots, are impinged, such as by the vertebral column or foreign matter. Additional scans, such as CT or MRI, may also be conducted in conjunction with PET or SPECT scans, to provide additional information, such as the structure and relative positioning of elements of the vertebral column. In one embodiment, this method may be applied to a surgical procedure to image the spinal region intraoperatively.

In another embodiment, myelination level is accessed in vivo by imaging a radioisotope derivative of an agent, which binds specifically to myelin basic protein. The agent is administered parenterally to a subject diagnosed with, or suspected of having, a myelin-associated neuropathy. After binding to myelin basic protein, and clearance from tissue that does not contain myelin basic protein without eliminating specific myelin basic protein binding, components of the central or peripheral nervous system may be imaged by a method suitable for in vivo imaging of the radioisotope. Such methods include PET and SPECT. By inspection of the imaging results, the clinician may determine the amount of myelination, as reflected by levels and anatomical localization of signal emitted by the radioisotope derivative of the agent and detected by the appropriate imaging methodology. In certain embodiments the agent is a radioisotope derivative of the compound of Formula I.

To determine whether myelination in the patient may be deficient, myelination levels may be compared to those exhibited by a subject or subjects believed or known not to be suffering from a myelin-associated neuropathy. In another embodiment, rates of demyelination or remyelination may be determined. Following treatment with a known or suggested therapeutic agent believed or anticipated to prevent or slow demyelination or to promote remyelination in patients suffering from myelin-associated neuropathies, myelination levels are evaluated by performing the imaging over time in the patients treated with the therapeutic agent. The imaging may be performed at different points of time and the level of myelination at one time point compared to that of another.

A positive result suggestive of a myelin-associated neuropathy may be one in which the decrease of myelin basic protein of the subject, compared to a baseline measurement of myelin basic protein, in a control sample is statistically significant. The control sample may be from a similar sample free of a myelin-associated neuropathy or from the same subject with measurements taken over time.

In yet another embodiment, a biopsied mammalian tissue sample, or a tissue sample cultured in vitro, may be contacted with an agent specific for binding to myelin basic protein. The agent may comprise the compound of Formula I, a $^{13}$C enriched compound of Formula I, or a $^{19}$F-labeled-derivative of Formula I. Contacting with the agent may be used to determine the location, presence, or amount of myelin basic protein in the tissue sample. The tissue sample may be sampled from a subject that has been experimentally manipulated so as to serve as a verified or purported model of myelin-associated neuropathy, or that has received at least one therapeutic agent verified as, or purported to be, a treatment for myelin-associated neuropathy. The therapeutic agent may be associated with the preclinical evaluation or basic neuroscience research aimed at studying the function and process of myelination, and the dysfunction and repair of myelin.

Fresh frozen cryostatic sections, or fixed or embedded sections or samples, of the biopsy or culture tissue sections, may be contacted with an agent specific for binding to myelin basic protein. The samples may be prepared using various sectioning techniques such as microtome, vibratome, or cryostat preparation. The agent may comprise the compound of Formula I, or a $^{13}$C enriched compound of Formula I, or an $^{19}$F-labeled-derivative of Formula I After binding to myelin basic protein, the sample may be washed in a manner and medium suitable to remove any unbound and non-specifically bound label from the sample, without eliminating specific binding to myelin basic protein.

Any of a number of detection, visualization, or quantitation techniques, including but not limited to fluorescence microscopy, laser-confocal microscopy, cross-polarization microscopy, autoradiography, MRI, MRS, or other applicable methods, or any combination thereof, may be then be used to assess the presence or quantity of an agent having specific binding to myelin basic protein in the tissue sample and may represent the presence or amount of myelin basic protein. In certain embodiments, the agent may comprise the compound of Formula I, a $^{13}$C enriched compound of Formula I, or a $^{19}$F-labeled-derivative of Formula I. The labeling with, and detection, visualization, or quantitation of the an agent, may also be performed in conjunction with labeling with, and detection, visualization, or quantitation of at least one other compound that specifically binds a substance other than myelin basic protein.

EXAMPLES

The following non-limiting Examples are shown and describe various embodiments of the present invention.

Example 1

Preparation of Nerve Tissue Sections

Various nerves including sciatic, femoral, brachial plexus, trigeminal, optic, and penile were harvested from male Sprague Dawley rats or male CD-1 mice. Tissue was fixed by perfusion and/or post-fixation with formalin. Following post-fixation, tissue was cryoprotected in a 20% sucrose solution made in phosphate buffered saline (PBS). Nerves were then flash-frozen using methanol and dry ice in OCT media. In some cases, PVDF membranes were used to help keep the nerves vertical in the OCT media. Thin sections (5-10 um) were sliced on a Leica microtome and stored in a −80° C. freezer prior to staining with antibodies or small molecule compounds.

Example 2

Histological Evaluation of Nerve Tissue Sections by Antibody

Some nerves were stained for hematoxylin and eosin in order to identify basic nerve morphology. Serial sections of the nerves were stained for a panel of myelin proteins; including myelin basic protein (MBP), myelin protein zero (MPZ), myelin associated glycoprotein (MAG), and peripheral myelin protein 22 (PMP22), and Schwann cell proteins 2',3'-Cyclic Nucleotide 3'-Phosphodiesterase (CNPase) and S100. Antibody vendor, catalog number and dilutions are shown in Table I. The nerves were stained on an automated Ventana Discovery XT immunostainer (Roche). Non-paraffin tissues were pre-treated in Cell Conditioning Solution, CC1, (Ventana). The slides were then blocked in 10% serum (species determined by host of secondary antibody). The primary and secondary antibodies were applied via manual application and incubated with heat (37° C.) on the immunostainer for one hour with rinses in between. The slides were then removed from the immunostainer and rinsed in a Dawn dish detergent solution to remove the mineral oil from the slides. Slides were then coverslipped by Vectashield™ mounting media. All secondary antibodies were purchased from Jackson ImmunoResearch Laboratories and were either Cy3 or Cy5 conjugated and used at a dilution of 1:200. After cover slipping, the slides were imaged on a Zeiss Axioimager microscope at 20×, using the appropriate filter set for each secondary antibody.

TABLE I

Antibodies used in characterization of nerves

| Antibody | Vendor + Catalog # | Dilution |
|---|---|---|
| MBP | Abcam ab2404 | 1:50 |
| MPZ | Santa Cruz sc-18533 | 1:50 |
| MPZ | Abcam ab39375 | 1:100 |
| CNPase | Lab Vision/Thermo MS-349 | 1:50 |
| MAG | Millipore/Chemicon MAB1567 | 5-10 ug/mL |
| S100A1 | Lab Vision/Thermo MS-296 | 1:100 |
| PMP22 | Lab Vision/Thermo MS-1293 | 2-4 ug/mL |
| PMP22 | Abcam ab | 1:50 |

Example 3

Measurement of Optical Properties of the Small Molecule Fluorophores

The fluorophores agents were dissolved in dimethylsulfoxide (DMSO) to make a 10 mM stock solution. An aliquot was taken to prepare a 10 nm-1 uM fluorophore solution in methanol, water, or DMSO. Optical measurements from the three solvents were taken. Absorbance spectra were measured using a Perkin Elmer Lambda 20 UV/VIS spectrometer. Emission spectra were generated using a PTI steady state fluorimeter.

Example 4

Ex vivo Staining of Nerves by the Fluorophores

The fluorophores were dissolved in DMSO to make a 10 mM stock solution. Slides containing nerve tissue sections were rinsed three times with PBS. The tissue sections were incubated with a solution of 10 uM of each fluorophore diluted in either PBS or a mixture of 99 uL DMSO, 100 uL cremaphor, 600 uL rat serum, and 200 uL PBS for 20 minutes. The slides were then washed with PBS for 5 min three times, cover-slipped with Vectashield and imaged on a Zeiss Axioimager microscope at 200× magnification. A custom filter cube (excitation filter: 387 nm with 11 nm bandpass, 409 nm dichroic mirror; emission filter 409 nm long pass) was used to collect images for examination of morphology and for image analysis.

Co-staining of the nerves with the fluorophores and various myelin antibodies was also performed. These slides were stained on the Ventana Discovery XT using the same protocol described above with some modification. The fluorophore was added directly to the primary antibody solution for a final fluorophore concentration of 10 uM and a final antibody dilution from Table 1. The slides were imaged using the Zeiss Axioimager microscope at 20× and analyzed as follows: Raw tagged image format images were used in all cases. Within each image representing the fluorophore channel, several circular areas of interest were drawn representing nerve-containing tissues, adjacent tissues, and regions without tissues. All areas of interest were identical in size, and all regions of the image were represented. The identical, co-localized areas of interest were drawn in the secondary antibody channel. The average channel signal intensities from each areas of interest were plotted against each other. The secondary antibody channel was plotted on the X-axis and the agent channel was plotted on the Y-axis. Regression coefficients were then calculated.

Example 5

Isolation of Native Myelin Basic Protein from Rat Brain

Purified myelin basic protein from rat brain was used for further evaluation of fluorophore binding. Crude myelin was isolated using a modified procedure from *Current Protocols in Cell Biology* (2006) 3.25.1-3.25.19. Isolation of native myelin basic protein from crude myelin was performed following the protocol from *NeuroReport* 5 (994) 689-692. Briefly, three rat brains from male Sprague Dawley rats were dissected, placed in 72 ml cold 0.30 M sucrose solution, diced and homogenized. The homogenate was layered over an equal volume of a 0.83 M sucrose solution, subjected to ultracentrifugation at 75,000 g at 4° C. for 30 min, and crude myelin collected at the interface of the two sucrose solutions.

The collected myelin fraction was subjected to osmotic shock by homogenization in Tris-Cl buffer (containing 20 mM Tris-Cl, pH 7.45, 2 mM sodium EDTA, 1 mM dithiothreitol, and protease inhibitor cocktail). Additional Tris-Cl was added to a final volume of 228 ml. The suspension was centrifuged at 75,000×g, 4° C. for 15 min. The pellet was subjected to two more times of homogenization and ultracentifugation at 12,000 g, 4 C for 15 min each time. The pellet was resuspended in 72 ml of 0.3 M sucrose solution. An equal volume of 0.83 M sucrose solution was layered over the resuspended pellet and the entire sample subjected to ultracentrifugation at 75,000 g at 4 C for 30 min. Purified myelin was collected from the interface, and resuspended in 228 ml Tris-Cl buffer. Washout of excess sucrose was performed by additional homogenization in Tris-Cl buffer and centrifugation as described above.

The myelin pellet was resuspended in 5 volumes of Buffer 1 (containing cold 500 mM NaCl/20 mM Tris-HCl/2 mM B-mercaptoethanol, pH 8.5) for 30 min, and then centrifuged on a JA20 at 15,000 rpm for 20 min. This was repeated twice. The pellet was solubilized into 2% CHAPS solution, incubated on ice for 30 min, then centrifuged at 40,000 rpm for 45 min, on Beckman 42.1 rotor. The CHAPS extract was loaded onto a hydroxyapatite column (1.6×5 cm) that was pre-equilibrated with 1% CHAPS solution. Lipid-bound MBP was eluted in the non-adsorbed pass-thru fraction. The pass-thru fraction was concentrated using an Amicon filter YM3. The concentrate was loaded onto a spectra gel AcA 44 gel filtration column that was pre-equilibrated with Buffer 2 (containing 1% CHAPS, 20 mM Tris-Cl, pH 8.5, 1 mM beta-mercaptoethanol, 1 mM dithiothreitol, 0.5 mM EDTA, 0.5 mM EGTA, 1 mM 1, 10 phenanthroline, 1 mM zinc acetate). The lipid-bound MBP was concentrated, salted out using 50% ammonium sulfate, lyophilized, and stored under nitrogen at 4° C. The samples were run in a standard denaturing polyacrylamide gel electrophoresis and Western blot. Reagents and standards for gel electrophoresis were from Invitrogen. Commercially available mouse MBP (Sigma) was used as a control.

Example 6

Fluorophore Binding to Isolated Native Myelin Basic Protein

Spectramax fluorescent assay: 0.5 nmol of the fluorophore was pipetted into a low-fluorescence 96-well plate. Using a Spectramax M5 multi-modality plate reader (Molecular Devices), the absorbance was scanned as well as the emission properties when excited at the peak absorbance wavelength. 0.5 nmol (1 equivalent) and 2 nmol (4 equivalents) each of bovine serum albumin, and native MBP was added to the fluorophore, and the absorbance and emission properties of the fluorophore were re-measured.

Bligh-Dyer Extraction: A lyophilized sample of native MBP was reconstituted into 0.5% CHAPS buffered in 20 mM Hepes at pH 7.4 at a concentration of 1 mg/mL. Lipids were extracted from a 400-uL sample of this protein using the Bligh-Dyer extraction method. Briefly, to each 200 uL protein sample, 750 uL of chloroform:methanol (1:2, v:v) was added and the sample vortexed well. Then, 250 uL of chloroform was added and the sample was vortexed. Next, 250 uL of distilled water was added and the sample was vortexed again followed by a 5 minute centrifugation spin at 1000 g. The bottom fraction (lipid fraction) was collected and dried under nitrogen before being reconstituted into the appropriate buffer for experiments. The lipid fraction was tested in the Spectramax fluorescence assay described above to rule out specific binding of the agents to the lipid component of MBP.

Example 7

In Vivo Imaging

CD-1 mice (25-40 g), housed in an AAALAC-compliant facility, were weighed and anesthetized by induction and maintenance on 2.5% Isoflorane. Animals were placed on their backs on a warming pad. With one hand the skin was held taut while 50 uMoles/kg of agent in Formulation 1 (100% DMSO and centrifuged at 10,000 g for 20 min) or Formulation 2 (10% DMSO, 5% Chremophor EL™, 75% mouse serum in phosphate buffered saline, centrifuged at 10,000 g for 20 min) was injected intraperitoneally or intravenously (in Formulation II only) with a 300 ul syringe equipped with a 30 gauge needle. The animals were allowed to recover from anesthesia and assume normal activity for four hours. At that time they were then anesthetized by induction and maintenance on 2.5% Isoflorane. They were injected as above with 100 ul of Fatal Plus (pentobarbital). The thoracic cavity and abdomen were accessed. The inferior vena cava was severed and 12 ml of phosphate buffered saline was infused via cardiac puncture at approximately 1 ml per minute followed by 12 ml of phosphate buffered formalin. Key nerves were exposed and imaged using a Zeiss Lumar V.12 surgical microscope equipped with filter sets appropriate for the fluorophore.

In some cases, ex vivo histological evaluation of nerve tissue sections was performed following in vivo imaging. Key nerves were resected, post-fixated with formalin overnight at 4 degrees celsius, and then cryoprotected in a 20% sucrose solution made in phosphate buffered saline. Nerves were then flash-frozen using methanol and dry ice in OCT media. Thin sections (5-10 um) were sliced on a Leica microtome and stored in a −80 freezer prior to staining with antibodies. The procedure for staining with antibodies was as described above.

Example 8

Synthesis of Intermediates for Formulas I-IV

Various compounds were synthesized and tested for specific binding to in vitro or in vivo samples containing myelin. The compounds were categorized based on the substituents pattern shown in Table II. BMB and BDB were used to compare binding and optical properties.

TABLE 2

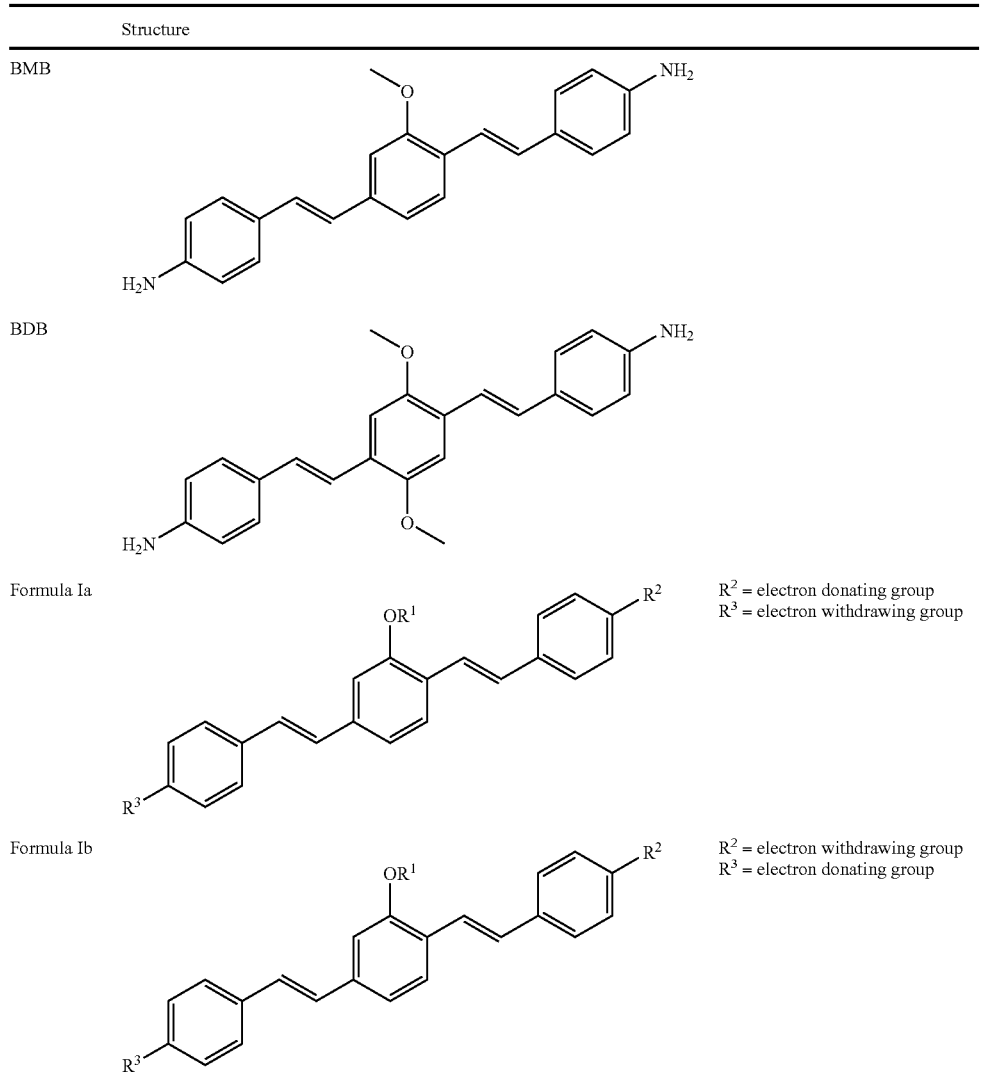

TABLE 2-continued

| Structure | |
|---|---|
| Formula II 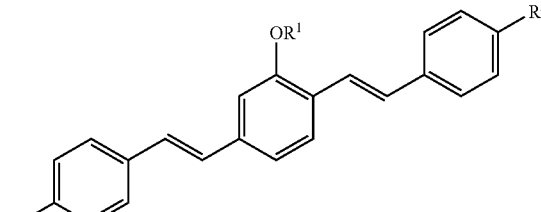 | R² = electron donating group |
| Formula III 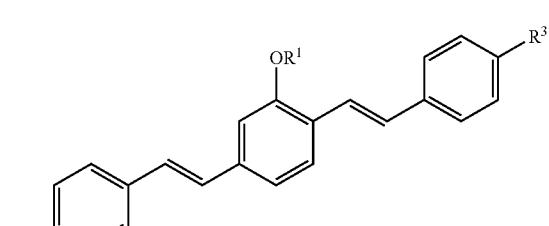 | R³ = electron withdrawing group |

As shown, Formula Ia and 1b have the preferred structures. Formula Ia represents structure whereby $R^2$ is an electron donating group on a fully conjugated substituent in the ortho position relative to the $OR^1$ group. $R^3$ is an electron withdrawing group on a fully conjugated substituent in the meta position relative to the $OR^1$ group and para to the $R^2$ substituted group.

Formula 1b are those compounds wherein the position of the electron donating group and the electron withdrawing group are reversed whereby $R^2$ is an electron-withdrawing group on a fully conjugated substituent in the meta position relative to the $OR^1$ group. $R^3$ is an electron donating group on a fully conjugated substituent in the ortho position relative to the $OR^1$ group and para to the $R^2$ substituted group.

Formula III represents compounds having two electron donating groups. Formula IV represents those compounds having two electron withdrawing groups.

General Synthetic Scheme

The introduction of the terminal amino moiety was effected via the use of the new building block 4-t-butoxycarbamoylbenzyl phosphonate, prepared according to the scheme below.

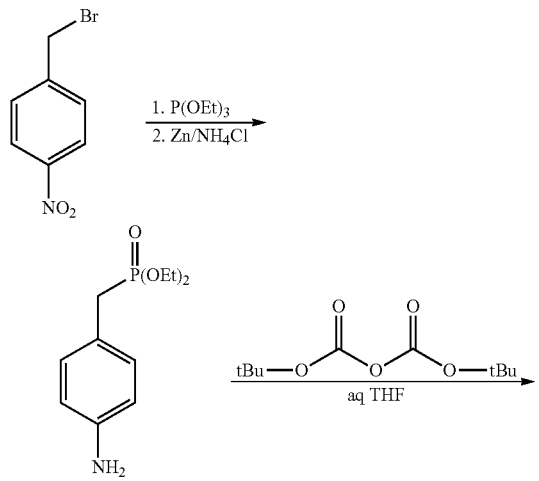

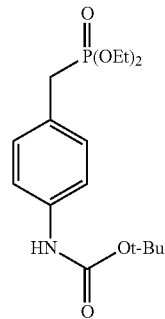

General procedure for the Horner-Wittig olefination: To a dry vial containing the aldehyde and the phosphonate (1 equivalent functional groups each) was added dry tetrahydrofuran (5 ml/mmol, equivalent to 0.2 M reactant concentration; for bis-functional substrates, additional THF may be needed later in the course of the reaction to solubilize the resulting potassium diethylphosphate). Potassium tert-butoxide (1.2 eq./phosphonate group) was then added and the mixture was heated to 60° C. under $N_2$ and monitored by GC-MS or LC-MS. Most reactions proceeded to completion within 1.5 hrs under these conditions. The reaction mixture was then concentrated using a rotoevaporator, diluted with brine and extracted with dichloromethane. The dried extract was concentrated, the crude product adsorbed on silicagel and purified by MPLC with hexanes-ethyl acetate, hexanes-dichloromethane or dichloromethane-methanol gradient.

Diethyl-4-aminobenzylphosphonate: To a solution of diethyl-4-nitrobenzylphosphonate (283 mg, 1.03 mmol) in acetone-water (2.9 ml/0.6 ml) was added Zn dust (270 mg, 4 eq.) followed by ammonium chloride (330 mg, 6 eq.). The reaction was warmed up to about 45° C. then returned to room temperature within 15 minutes. GC-MS indicated complete conversion by 30 minutes. Ammonium hydroxide (2 ml, 25%) and ethyl acetate (3 ml) were added, the mixture washed with brine (3 ml) and the organic layer separated. The aqueous layer was extracted with EtOAc twice, the combined organic layers were dried and the solvent was removed under reduced pressure. The orange oil was desiccated at 20 mtorr and 30° C. for 1 hr before being taken to the next step.

Diethyl-4-t-butoxycarbamoylbenzyl phosphonate: To a solution of diethyl-4-aminobenzylphosphonate (0.499 g, 2.05 mmol) in aqueous THF (6.5 ml THF/1.6 ml water, 80/20 v/v) was added tert-butyloxycarbonyl, anhydride (495 mg, 1.1 eq.) and sodium bicarbonate (258 mg, 1.5 eq). The mixture was stirred at room temperature for 20 hrs. Brine (5 ml) was added and the mixture was extracted with EtOAc, dried and purified by MPLC (hexanes/ethyl acetate 45-100%). LC-MS (ESI$^+$): 366 (M+Na$^+$); 385 (M+CH3CN+H$^+$). $^1$H-NMR (CDCl$_3$): 1.23 (t, J=12 Hz, 6H); 1.52 (s, 10H); 3.12 (d, J=75 Hz, 2H); 4.04 td, J=7 Hz, 0.8 Hz, 4H); 6.58 (brs, 0.85H); 7.22 (dd, J=6 Hz, 0.8H, 2H); 7.36 (d, J=6 Hz, 2H).

4-Bromo-2-methoxybenzaldehyde dimethylacetal: To a solution of 4-bromo-2-methoxybenzaldehyde (5.2 g, 24.2 mmol) in methanol (20 ml) and trimethylorthoformate (14 ml, 5.5 eq.) was added p-toluenesulfonic acid (46 mg, 0.01 eq.) and the mixture was refluxed for 3 hr. Potassium carbonate (125 mg, 0.03 eq.) and silicagel was added, the solvent was removed under reduced pressure and the solid residue packed into a loading column and purified by MPLC (hexanes-ethylacetate 40-80% gradient). MS (EI$^+$): 262, 260 (1/1, M$^+$, 10%); 231, 229 (1/1, 90%); 215, 213 (1/1, 10%); 199, 170, 150, 118, 92, 75, 45 (100%).

4-Formyl-2-methoxybenzaldehyde dimethylacetal: To a solution of the aryl bromide above (5.99 g, 22.9 mmol) in dry ether (65 ml) at −30° C. was added a trace of 1,10-phenantroline, followed by a solution on n-BuLi 2.6 M in hexanes. Upon the addition of 1.2 ml, all moisture was used up as indicated by the orange-pink coloration. At this point 10 ml of n-BuLi solution were added (1.09 eq.), the mixture was warmed up to 0° C. and stirred at this temperature for 45 min. The light pink-orange suspension was cooled to −78° C. and treated with N-formylpiperidine (5 ml, 1.95 eq.) dropwise. The mixture was allowed to warm to room temperature and stirred for 1 hr at 20° C. Water was added and the organic layer washed with water three times and brine one time. The aqueous waste was extracted with ether and the combined organic layers were dried and concentrated under reduced pressure to give the desired product in nearly quantitative yield, 99% pure by GC-MS. MS (EI$^+$): 210 (10%, M$^+$); 179 (100%); 163, 135, 119, 91, 75, 45 (90%).

(E)-4-(4-(dimethoxymethyl)-3-methoxystyryl)benzonitrile: To a dry vial containing 4-formyl-2-methoxybenzaldehyde dimethylacetal (452 mg, 2.15 mmol) and 4-cyanobenzyl diethylphosphonate (545 mg, 1 eq.) in THF (12 ml) was added potassium t-butoxide (290 mg, 1.2 eq.). The mixture turned green and became gel-like within 10 minutes at room temperature. The mixture was refluxed gently for 10 minutes, diluted with brine and extracted with ethyl acetate. The solution was dried and the crude product flushed through a silicagel SPE cartridge with EtOAc. MS (EI$^+$): 309 (12%, M+); 278 (100%); 262, 234, 219, 204 (15%), 190 (20%), 165, 139, 75, 45 (95%).

(E)-4-(4-formyl-3-methoxystyryl)benzonitrile: To a solution of (E)-4-(4-(dimethoxymethyl)-3-methoxystyryl)benzonitrile (70 mg, 0.227 mmol) in aqueous THF (5 ml water/25 ml THF) was added p-toluenesulfonic acid (1 mg, 0.02 eq.) and the mixture was refluxed for 30 minutes. The mixture was concentrated under reduced pressure, extracted with EtOAc (3×), dried, and the solvent was removed in vacuum to give the desired product 99% pure by GC-MS. MS (EI$^+$): 263 (100%, M+); 246 (40%), 232, 216, 203 (60%), 190 (65%), 176, 140, 88.

Synthesis of Formula Ia Compounds tert-Butyl 4-(4-(4-cyanostyryl)-2-methoxystyryl)phenylcarbamate: To a dry vial was added (E)-4-(4-formyl-3-methoxystyryl)benzonitrile (142 mg, 0.54 mmol), diethyl-t-butoxycarbamoylbenzyl phosphonate (223 mg, 1.2 eq.) and dry tetrahydrofuran (3 ml). In a glove box, solid potassium t-butoxide (91 mg, 1.5 eq.) was added and the mixture was returned to the hood and heated to 60° C. for 90 min. The mixture was diluted with brine, extracted with EtOAc, dried, and purified by MPLC (hexanes/ethyl acetate). Yield: 224 mg (92%). MS (ESI$^+$): 452 (M$^+$); 475 (M+Na$^+$); 495 (M+CH$_3$CN+H$^+$).

4-(4-(4-Aminostyryl)-3-methoxystyryl)benzonitrile), (Formula Ia, R$^1$=CH$_3$ R$^2$=NH$_2$, R$^3$=CN): To a solution of tert-butyl 4-(4-(4-cyanostyryl)-2-methoxystyryl)phenylcarbamate (27.4 mg, 60.6 mmol) in dichloromethane (4.8 ml) was added trifluoroacetic acid (1.2 ml) and the mixture was stirred at room temperature for 3 hrs. The solvent was removed under reduced pressure, neutralized with a solution of sodium bicarbonate and extracted with EtOAc. The crude product was purified by MPLC (1% triethylamine in dichloromethane, 0-2.5% gradient methanol) to give the desired dye>98% pure by LC-MS. MS (ESI$^+$): 352 (M$^+$); 353 (M+H$^+$); 394 (M+CH$_3$CN+H$^+$). $^1$H-NMR (aceone-D6): 3.97 (s, 3H); 4.8-4.95 (br s, 1H); 5.67 (d, J=20 Hz, 1H); 6.70 (dd, J=4 Hz, 0.4 Hz, 2H); 7.14-7.40 (m, 8H); 7.76-7.83 (m-q-like, 4H).

Synthesis of Methyl 4-(4-(4-Aminostyryl)-3-methoxystyryl) benzoate (Formula Ia, R$^1$=CH$_3$, R$^2$=NH$_2$, R$^3$=CO$_2$Me)

Dimethyl-4-carbomethoxylbenzyl phosphonate: A mixture of 4-bromomethyl methyl benzoate (2.29 g, 10 mmol) and trimethylphosphite (5.9 ml, 5 eq.) was heated while stirred at 100° C. for 1.5 hrs. The excess phosphite was removed under reduced pressure and the residual oil (99% pure by GC-MS) was used in the next step without further purification. MS, m/e: 258 (M$^+$, 50%); 227 (60%); 198 (90%); 162 (35%); 149 (100%); 121 (42%); 118 (40%); 109 (58%); 90 (50%).

Methyl (E)-4-(4-(dimethoxymethyl)-3-methoxystyryl) benzoate: The compound was prepared according to the general Horner-Wittig methodology, from 4-formyl-2-methoxybenzaldehyde dimethylacetal (630 mg, 3 mmol), dimethyl-4-carbomethoxylbenzyl phosphonate (775 mg, 1 eq.) using tBuOK (404 mg, 1.2 eq.) as base in anhydrous THF (15 ml); the mixture was heated at 70 C for 90 minutes then worked up as described previously and purified by MPLC with hexanes/ ethyl acetate 0-30% gradient. Yield: 795 mg (76%). MS, m/e: 342 (M$^+$) 15%; 311 (M$^+$-MeO, 100%); 294 (5%); 234 (4%); 164 (12%); 139 (10%).

Methyl (E)-4-(4-formyl-3-methoxystyryl)benzoate: The compound was prepared by acid hydrolysis of methyl (E)-4-(4-(dimethoxymethyl)-3-methoxystyryl)benzoate, according to the procedure described for the synthesis of (E)-4-(4-formyl-3-methoxystyryl)benzonitrile; Thus, from 258 mg acetal (0.75 mmol), in the presence of 1.7 mg pyridinium triflate in a 6 ml THF/1.5 ml water solution, was obtained upon refluxing for 30 minutes and cooling, the desired product in nearly quantitative yield (220 mg) as a mass of long, fluffy needles. MS, m/e: 296 (M+, 100%); 264 (15%); 234 (35%); 164 (45%); 138, 114, 82 (6%).

tert-Butyl-4-(4-(4-carbomethoxystyryl)-2-methoxystyryl) phenylcarbamate: To a dry vial was added methyl (E)-4-(4-formyl-3-methoxystyryl)benzoate (222 mg, 0.75 mmol), diethyl-t-butoxycarbamoylbenzyl phosphonate (262 mg, 1.02 eq.) and dry tetrahydrofuran (4 ml). In a glove box, solid potassium t-butoxide (101 mg, 1.2 eq.) was added and the mixture was returned to the hood and heated to 70° C. for 90 min. The mixture was diluted with brine, extracted with EtOAc, dried, and purified by MPLC (hexanes/ethyl acetate-10% dichloromethane, 5-80% gradient). Yield: 300 mg (82%). MS (ESI+): 485 (M+); 508 (M+Na+); 549 (M+CH$_3$CN+Na+).

Methyl 4-(4-(4-Aminostyryl)-3-methoxystyryl)benzoate) (Formula I, R$^1$=CH$_3$, R$^2$=NH$_2$, R$^3$=CO$_2$CH$_3$): To a solution of tert-Butyl-4-(4-(4-carbomethoxystyryl)-2-methoxystyryl)phenylcarbamate (300 mg, 0.62 mmol) in dichloromethane stabilized with 42 ppm amylene (48 ml) was added trifluoroacetic acid (12 ml) and the mixture was stirred at room temperature for 45 min. The solvent was removed under reduced pressure, the residue taken in dichloromethane, neutralized with a solution of sodium bicarbonate and the aqueous phase extracted with dichloromethane. The combined organic phases were dried over Na$_2$SO$_4$ and the solvent was removed under reduced pressure, giving the desired dye>98% pure by LC-MS. MS (ESI+): 386 (M+H+); 427 (M+CH$_3$CN+H+).

Synthesis of Formula Ib Compounds (E)-tert-butyl 4-(4-(dimethoxymethyl)-3-methoxystyryl)phenylcarbamate: To a dry vial containing 4-formyl-2-methoxybenzaldehyde dimethylacetal (408 mg, 1.93 mmol) and diethyl-4-t-butoxycarbamoylbenzyl phosphonate (668 mg, 1 eq.) in THF (10 ml) was added potassium t-butoxide (265 mg, 1.2 eq.) in a glove box. The mixture was sealed under N$_2$, heated to 70° C. and stirred at this temperature for 1 hr. To the cooled mixture was added triethylamine (0.5 ml), the crude product was diluted with ethyl acetate and adsorbed on silicagel. The product acetal was purified by MPLC using hexanes/ethyl acetate 10-60% gradient. MS (ESI+): 422 (M+23, M+Na+). Yield: 451.4 mg (66%).

(E)-tert-butyl 4-(4-formyl-3-methoxystyryl)phenylcarbamate: To a solution of the acetal (451.4 mg, 1.13 mmol) in THF/H$_2$O (6.6 ml of 80/20 v/v, 5.3 ml THF/1.3 ml H$_2$O) was added a catalytic amount of pyridinium triflate (2.6 mg, 0.01 eq.) and the mixture was heated to 60° C. for 30 minutes. LC-MS at this point (water/acetonitrile, 0.1% ammonium formate) indicated complete conversion without loss of the Boc group. The crude mixture was adsorbed on silicagel under reduced pressure and purified by MPLC (silica) 20-60% B gradient, where solvent A was hexanes and solvent B was 10% CH$_2$Cl$_2$ in ethyl acetate. Yield: 319.1 mg (46.8%). H-NMR (acetone-D6): 1.52, (s, 9H); 4.06 (s, 3H); 7.24 (1H, d, J=16 Hz); 7.31 (1H, d, J=6 Hz); 7.42-7.48 (m, 2H); 7.62 (4H, dd, J=15, 6 Hz); 7.74 (1H, d, J=6 Hz); 8.58 (s, 1H); 10.42 (s, 1H).

tert-Butyl 4-(4-(4-cyanostyryl)-3-methoxystyryl)phenylcarbamate: To a dry vial was added (319.1 mg, 0.903 mmol), diethyl-4-cyanobenzyl phosphonate (233 mg, 1.02 eq.) and dry tetrahydrofuran (4.7 ml). In a glove box, solid potassium t-butoxide (121.5 mg, 1.2 eq.) was added and the mixture was returned to the hood and heated to 60 C for 75 min. The crude mixture was diluted with ethyl acetate, adsorbed on silicagel and purified by MPLC with hexanes (A)/ethyl acetate-10% dichloromethane (B), 20-85% (B) gradient to give the title compound as a lemon-yellow solid (384 mg, 94%). MS (ESI+): 452 (M+); 475 (M+Na+); 495 (M+CH$_3$CN+H+). H-NMR (acetone-D6): 1.51 (s, 9H); 4.01 (s, 3H); 7.15-7.28 (m, 2H); 7.3-7.42 (m, 2H); 7.54-7.65 9 m, 4H); 7.68-7.84 (m, 7H); 8.53, (s, 1H); C-NMR (acetone-D6): 55.14, 79.26, 100.81, 118.26, 124.37, 127.12, 128.96, 132.45, 139.64, 142.82, 152.73, 157.70.

4-(4-(4-aminostyryl)-2-methoxystyryl)benzonitrile (Formula Ib, R$^1$=CH$_3$, R2=NH$_2$, R3=CN): To a solution of the carbamate described above (200 mg, 0.44 mmol) in 35 ml dichloromethane stabilized with 42 ppm amylene was added trifluoroacetic acid (8.8 ml) and the mixture was stirred at room temperature for 45 minutes. Analysis of an aliquot indicated complete conversion. The reaction mixture was evaporated to dryness under reduced pressure, the residue was taken in dichloromethane, washed with aqueous NaHCO$_3$, the organic phase was separated, and the crude product was adsorbed on silicagel and purified by MPLC using hexanes (A)/dichloromethane+1% triethylamine+1% MeOH (B) 10-50% (B) gradient. MS (ESI+): 352 (M+); 353 (M+H+); 394 (M+CH$_3$CN+H+).

Synthesis of Formula II Compounds

Methyl 4-(4-(4-dimethylaminostyryl)-3-methoxystyryl)benzoate (Formula I, R$^1$=CH$_3$, R$^2$=N(CH$_3$)$_2$, R$^3$=CO$_2$CH$_3$): To a solution of the aminoester (Formula I, R$^1$=CH$_3$, R$^2$=NH$_2$, R$^3$=CO$_2$CH$_3$) (231 mg, 0.6 mmol) in 1,2-dichloroethane (6.1 ml) was added an aqueous solution of formaldehyde (1.44 ml; 37%, 3 eq.), glacial acetic acid (0.34 ml, 10 eq.) and sodium triacetoxyborohydride (385 mg, 3 eq.) and the mixture was stirred at room temperature for 16 hrs. Water (12 ml) was added. The organic phase was separated, the aqueous phase was extracted with dichloromethane, the combined organic phases dried over sodium sulfate and the solvent was removed under reduced pressure. Yield: 240 mg (98%). MS (ESI+): 414 (M+H+); 455 (M+CH$_3$CN+H+).

Methyl 4-(4-(4-dimethylaminostyryl)-3-methoxystyryl)benzoic acid (Formula II, R$^1$=CH$_3$, R$^2$=N(CH$_3$)$_2$, R$^3$=CH$_2$OH) To a solution of Methyl 4-(4-(4-dimethylaminostyryl)-3-methoxystyryl)benzoate described above (240 mg, 0.58 mmol) in anhydrous THF (6 ml) at 0° C. was added LiAlH$_4$ (35 mg; 95%, 1.5 eq.) and the mixture was stirred for 35 minutes. Analysis of an aliquot indicated complete, clean, conversion to the desired product (Formula III, R$^1$=CH$_3$, R$^2$=N(CH$_3$)$_2$, R$_3$=CH$_2$OH). Under vigorous stirring, at 0° C., was then added carefully an aqueous solution of Rochelle salt (10 ml), the mixture was extracted with ethyl acetate, dried and evaporated under reduced pressure. The residue was adsorbed on silicagel and purified by MPLC with hexanes/ethyl acetate 30-60% gradient. Yield: 204 mg (92%). MS (ESI+): 386 (M+H+); 427 (M+CH$_3$CN+H+).

General Scheme:

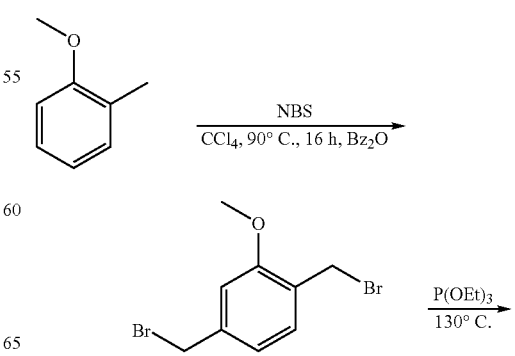

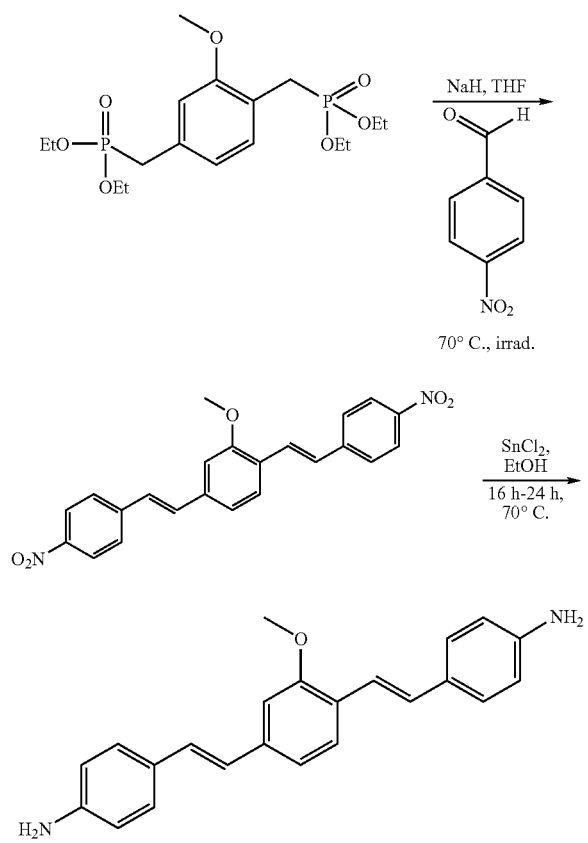

Synthesis of Formula III Compounds

Synthesis of 1,4-bis(bromomethyl)-2-methoxybenzene: To a suspension of NBS (N-bromosuccinimide) (34.5 g, 190 mmol) in anhydrous $CCl_4$, benzoyl peroxide (50 mg) was added. The reaction suspension was heated at refluxing $CCl_4$ under nitrogen atmosphere and stirred overnight. The reaction was followed by GCMS (100 ul in 2 ml of CH2Cl2). After 1 h of heating, the reaction mixture was clear but GCMS showed very little conversion. Benzoyl peroxide (100 mg) was added again and refluxed for another 13 h. The reaction was then analyzed by GCMS. The resulting reaction was filtered over a Buchner funnel to remove succinimide as well as unreacted NBS. Removal of the solvent afforded a light brown cake. The cake was then washed with hexane (3×200 ml). The washings were combined and evaporated to afford a white amorphous solid (6.83 g, 26%). GCMS (m/z): 293 (M+), 213 (molecular ion), 133. (Short 15 min method, 75-300° C., 20° C./min ramp for 10 min, hold at 300° C. for 5 min).

Synthesis of tetraethyl (2-methoxy-1,4-phenylene)bis(methylene)diphosphonate: The reaction was set up in a 7 ml vial and capped loosely to avoid overpressure. Dibenzylbromide was introduced in the 7 ml vial, with 12 ml of $P(OEt)_3$ (3 equivalents.) It was then heated up in a heating block at 135° C. overnight. GCMS showed the complete conversion of the starting material. GCMS (m/z): 408 (M+), 271, 215, 104. (Retention time: 8.9 min).

Synthesis of 4,4'-(1E,1'E)-2,2'-(2-methoxy-1,4-phenylene)bis(ethene-2,1-diyl)bis(nitrobenzene) (Formula III $R^1$=CH3, $R^2$=$R^3$=NO2): To an oven dried 3-neck round-bottomed flask charged with NaH (150 mg, 4.17 mmol) was added a solution of diphosphonate (1.0 g, 2.45 mmol). The reaction mixture was first heated up using a heating block and a GE Sunlamp 275 W under nitrogen. The temperature was adjusted to 70° C. using a variable transformer. The reaction was quenched after 16 h of refluxing by careful addition of ice water. Evaporation in vacuum followed by recrystallization of the resulting dark oil afforded the compound as a red crystalline solid. (40%, 410 mg). (For a scale of 0.5 mmol of starting bisphosphonate, a yield of 84% was obtained). GCMS and $^1$HNMR confirmed the identity of the product.

Synthesis of BMB: 4,4'-(1E,1'E)-2,2'-(2-methoxy-1,4-phenylene)bis(ethene-2,1-diyl)bis(nitrobenzene) (1.0 g, 2.49 mmol), zinc dust (2.87 g, 19.8 mmol), and NH4Cl (1.7 g) were suspended in a mixture of acetone and water (1.5 L) (4:1) and was refluxed for 1.5 h under inert atmosphere and vigorous stirring. The reaction mixture was then cooled down, filtered and reduced in vacuum. The pH was adjusted to 12-13 (pH paper) by adding NaOH pellets and then was extracted with EtOAc (2×300 ml) and CH2Cl2 (2×300 ml). The combined organic layers were dried over Na2SO4, filtered and evaporated to afford a red viscous oil (2.08 g). BMB was then purified by MPLC using a mixture of hexanes, ethyl acetate and DIPEA (gradient: 20-100% of EtOAc) over $SiO_2$. The fractions corresponding to the major peaks were collected, combined and evaporated to afford a red orange solid (650 mg, 72%). $^1$H NMR confirmed the identity of BMB.

A radioisotope derivative of the compound of Formula I may be prepared and imaging accomplished through radio-imaging. Alternatively, a $^{13}$C enriched compound of Formula I or a $^{19}$F-labeled derivative of Formula I may be prepared. In certain embodiments, a compound of formula I having $R^1$=$CH_2CH_2OTs$ (where Ts is tosylate) may be used as precursor for radiolabeling with $^{18}$F (PET) and $^{124}$I (SPECT); other choices for the tosylate leaving group may be selected as generally known in the radiolabeling practice. Additionally, a compound of formula I where $R^1$=$CF_3$ or $C_1$-$C_4$ perfluoroalkyl may be used for $^{19}$F-based MRI and a compound of Formula I where $R^1$=$^{13}$C-methyl or $^{13}$C-enriched $C_1$-$C_4$ alkyl may be used for $^{13}$C-based MRI. These compounds may be prepared following the general methodology described herein, or may be accessible via a precursor Formula I where $R^1$=H via nucleophylic alkylation.

Alternatively, a $^{13}$C labeled derivative of the compound of Formula I may be prepared by alkylating the amino functionality of the compound of formula I with $^{13}$C enriched methyl iodide or a similar $C_1$-$C_4$ alkylating agent. A $^{19}$F derivative of the compound of Formula I may be prepared by alkylating the amino functionality of the compound of Formula I with a $C_1$-$C_4$ fluoro- or perfluoroalkyl halide, mesylate, or tosylate, by reacting with a fluoroacyl halide such as pentafluorophenyl benzoyl chloride to yield the corresponding amide or by reductive amination where the carbonyl component bears a $^{13}$C or $^{19}$F moiety. In other embodiments, the amine moiety of Formula I may be alkylated to produce a 2-hydroxyethyl derivative which can be used via its tosylate or mesylate as a precursor for the radiolabeling with $^{18}$F (PET) and $^{124}$I (SPECT).

Results and Observations

TABLE III

Fluorescence excitation and emission peaks of Select Compounds

| Formula | R1 | R2 | R3 | Nerve binding, ex vivo | Excitation (MeOH) | Emission (MeOH) | Excitation (H2O) | Emission (H2O) | Excitation (DMSO) | Emission (DMSO) |
|---|---|---|---|---|---|---|---|---|---|---|
| BMB | | | | +++ | 381 | 492 | 380 | 526 | 408 | 495 |
| BDB | | | | +++ | 402 | 494 | 423 | 527 | 422.5 | 502 |
| Ia | $CH_3$ | $NH_2$ | CN | +++ | 395 | 592 | 380 | 578 | 417 | 623 |
| | | $NH_2$ | $CO_2CH_3$ | +++ | 395 | 510 | 390 | Undetectable | 410 | 530 |
| | | $N(CH_3)_2$ | CN | + | 395 | 495 | 393 | 594 | 412 | 518 |
| | | $N(CH_3)_2$ | $C=C(CN)_2$ | + | 408 | 550 | 382 | Undetectable | 467 | 580 |
| Ib | | $NH_2$ | CN | +++ | 394 | 592 | 388 | 574 | 415 | 615 |
| II | $CH_3$ | $NH_2$ | $NH_2$ | +++ | 381 | 492 | 380 | 526 | 408 | 495 |
| | | $N(CH_3)_2$ | $N(CH_3)_2$ | +++ | 399 | 497 | 364 | 530 | 416 | 511 |
| | | $OCH_3$ | $OCH_3$ | +++ | 381 | 431 | 357 | 510 | 392 | 460 |
| | | $SCH_3$ | $SCH_3$ | +++ | 371 | 434 | 363 | 494 | 381 | 445 |
| | | $N(CH_2)_2CH_3$ | $N(CH_2)_2CH_3$ | − | 411 | 497 | 410 | 527 | 424 | 508 |
| | | $N(CH3)2$ | $CH2OH$ | +++ | 382 | 530 | 366 | 530 | 400 | 550 |
| III | CH3 | NO2 | NO2 | − | 412 | 548 | 395 | 591 | 427 | 598 |
| | | CN | CN | + | 398 | 497 | 364 | 530 | 416 | 511 |
| | | CN | NO2 | − | 342 | 453 | 343 | 571 | 350 | 597 |

Fluorescence excitation and emission peaks of various compounds, and relative binding are shown in Table III.

Examination of the hematoxylin and eosin staining of nerve tissue sections revealed characteristic nerve morphology can be identified. Each nerve or nerve bundle appeared as a large circle or group of large circles within which smaller donut-shaped myelinated axons can be identified. Serial sections of a nerve were stained with different myelin protein antibodies, and the staining pattern and morphology compared with that of BMB.

Table IV summarizes the immunohistochemistry and BMB staining. A single + indicates a positive staining signal, but dissimilar pattern between the antibody and BMB staining. A +++ indicates a positive signal and similar morphology. A − indicates no staining signal. As shown in Table IV the myelin basic protein (MBP) most closely correlated with the staining pattern and morphology of BMB across all the different nerves tested.

TABLE IV

Summary of nerve immunohistochemistry compared to BMB staining

| Nerve | MPZ | MBP | CNPase | S100 | PMP22 | MAG | BMB |
|---|---|---|---|---|---|---|---|
| Brain Striatum | − | +++ | + | + | + | + | +++ |
| Sciatic | +++ | +++ | +++ | +++ | + | + | +++ |
| Femoral | + | +++ | − | + | + | + | +++ |
| Trigeminal | +++ | +++ | + | + | + | + | +++ |
| Optic | − | +++ | +++ | + | | | +++ |
| Brachial plexus | +++ | +++ | − | + | | | +++ |
| Penis | − | +++ | | | − | | +++ |

Figure 1B:
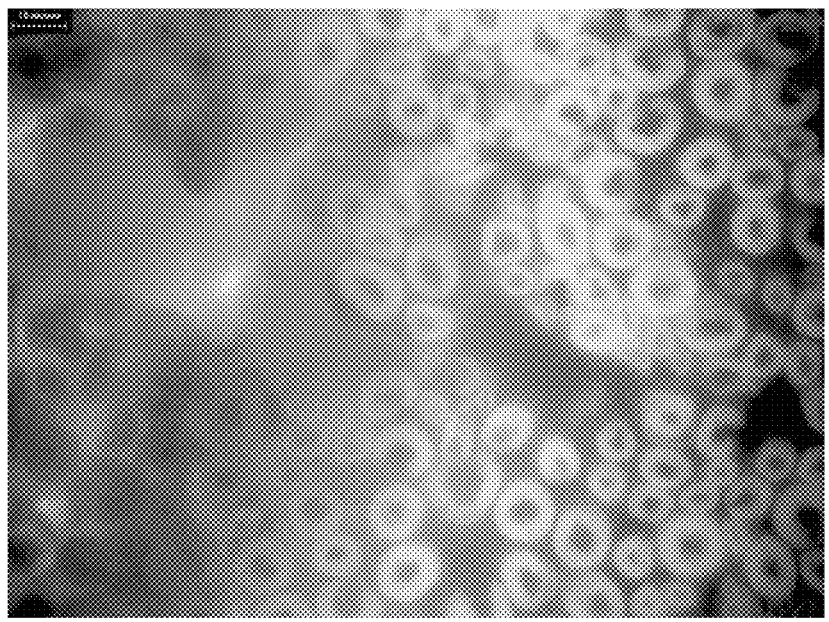
Figure 2:
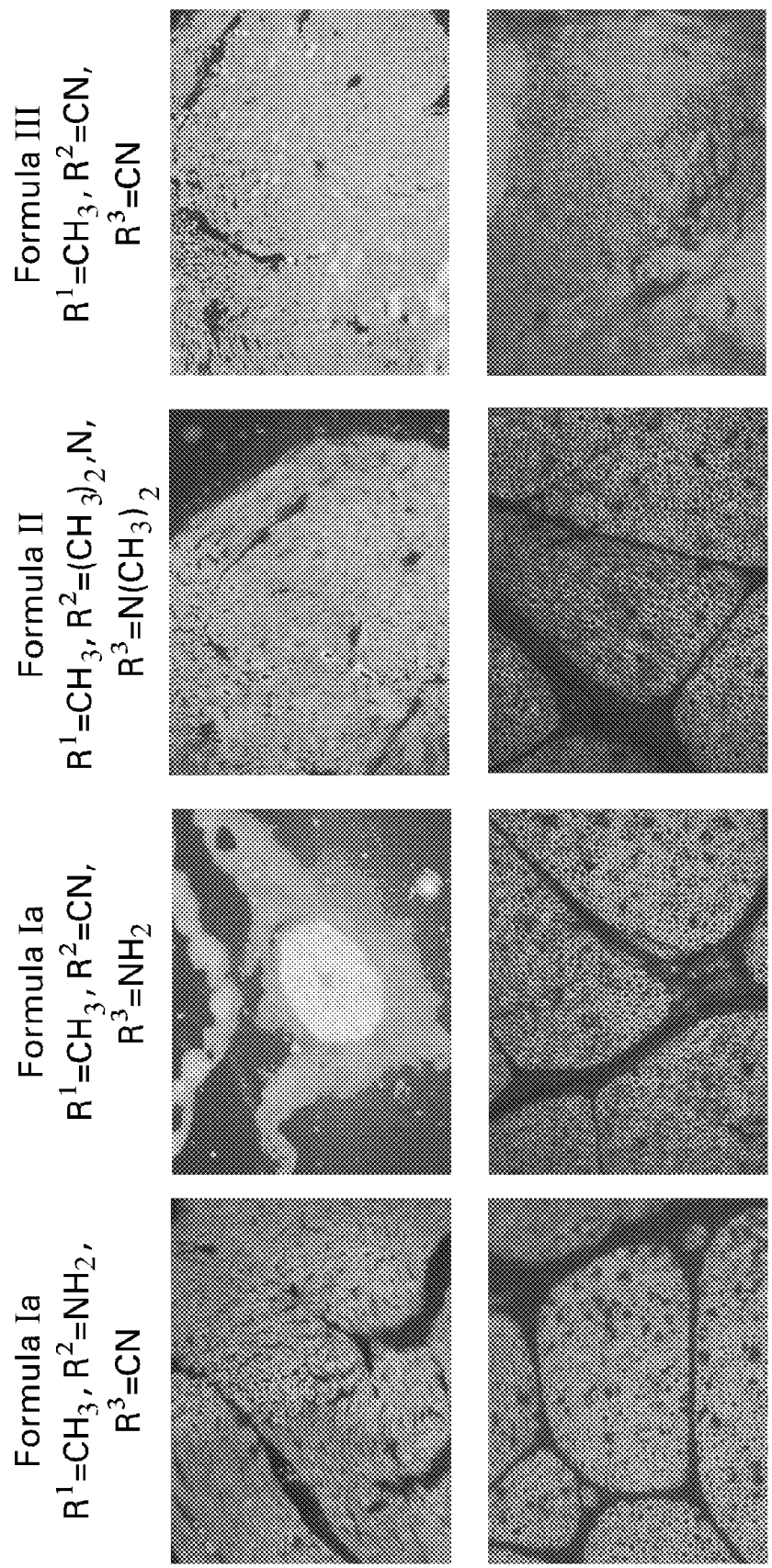
FIG. 2 shows results from ex vivo staining of rat sciatic nerve (top panel) and trigeminal nerve sections (bottom) by Formulas Ia, Ib, II, and III agents.

FIG. 1A shows staining of a section of trigeminal nerve with the MBP antibody, while FIG. 1B shows the trigeminal nerve staining with BMB. The results with BMB are the same as the MBP antibody. The donut-shaped structures are myelinated nerve fibers. FIG. 2 show representative images acquired when the sciatic and trigeminal nerve tissue sections were stained with examples of agents from Formula Ia, Ib, II, and III. The control slides containing the nerves with no agent (not shown) was negative under the same imaging conditions. As shown, staining with Formula Ia and Ib agents resulted in increased visualization of myelin basic protein as compared to Formula II and III agents.

Figure 3:
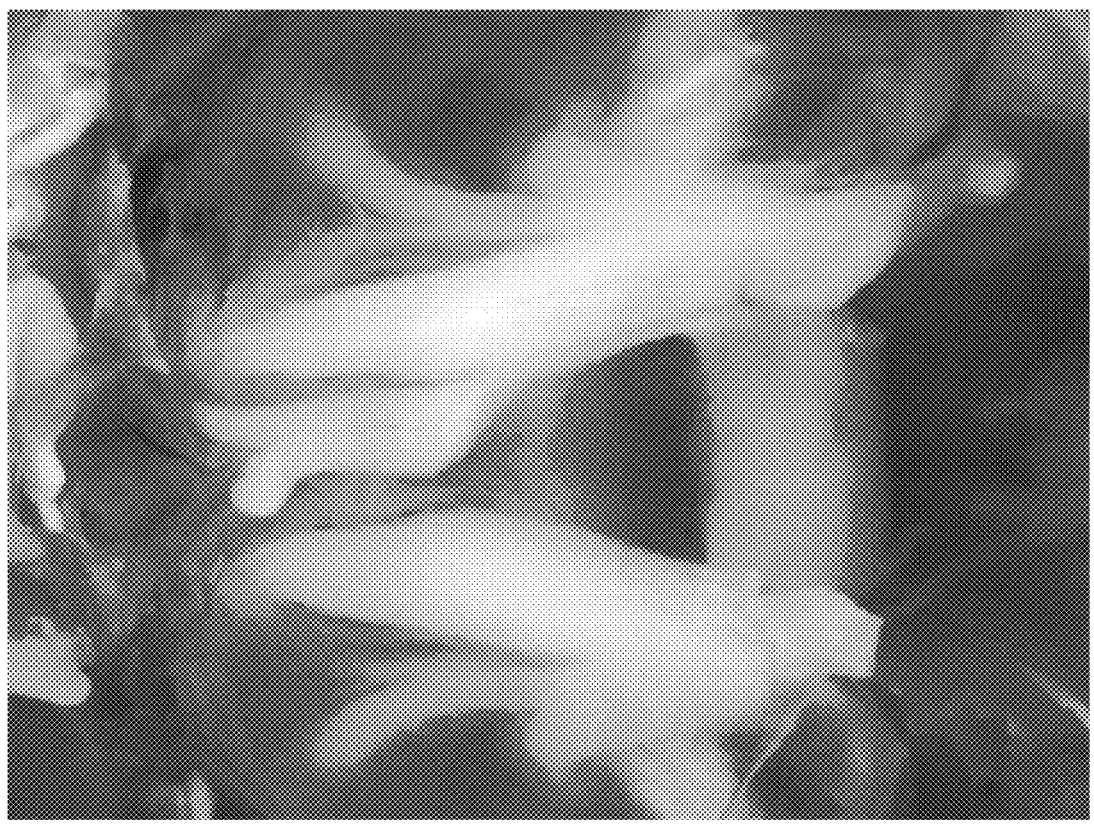
FIG. 3 shows results from fluorescence in vivo imaging of the trigeminal and optic nerves of a mouse treated with Formula Ia ($R1=CH_3$, $R^2=NH_2$ and $R^3=CN$).

When the agents were injected systemically to the pre-clinical animal model, in vivo imaging revealed that some of the agents localized to nerves in a number of tissues including the brachial plexus, facial nerve, trigeminal nerve, phrenic nerve, vagus nerve and optic nerve when administered systemically to a pre-clinical animal model. The adjacent muscle tissues had very low background binding. The nerves of the negative control animals, with no fluorophore administered, had no fluorescent signal. FIG. 3 shows fluorescent in vivo imaging of the trigeminal and optic nerves in the mouse surgical model by the Formula Ia ($R^1=CH_3$, $R^2=NH_2$ and $R^3=CN$). In vivo performance of the agents is a combination of several factors, including but not limited to agent myelin-binding property, blood nerve barrier penetration, metabolism, plasma binding, half-life, solubility, and clearance rate. Agents that did not stain nerve tissue sections in the ex vivo assay were typically not tested in vivo. Compounds of Formula Ia ($R^1=CH_3$, $R^2=NH_2$ and $R^3=CO2CH3$) and ($R^1=CH_3$, $R^2=NCH_3)_2$ and $R^3=CN$) did not stain nerves in vivo. Formula Ib ($R^1=CH_3$, $R^2=CN$ and $R^3=NH_2$) stained nerves in vivo. BMB stained nerves in vivo. Formula II ($R^1=CH_3$, $R^2=N(CH_3)_2$ and $R^3=N(CH_3)_2$), ($R^1=CH_3$, $R^2=OCH_3$ and $R^3=OCH_3$), ($R^1=CH_3$, $R^2=N(CH_2)_2CH_3$ and $R^3=N(CH_2)_2CH_3$) did not stain nerves in vivo. Formula II ($R^1=CH_3$, $R^2=SCH_3$ and $R^3=SCH_3$) precipitated at the injection. Formula II ($R^1=CH_3$, $R^2=N(CH_3)_2$ and $R^3=CH_2OH$) showed weak nerve signal in vivo.

Figure 4:
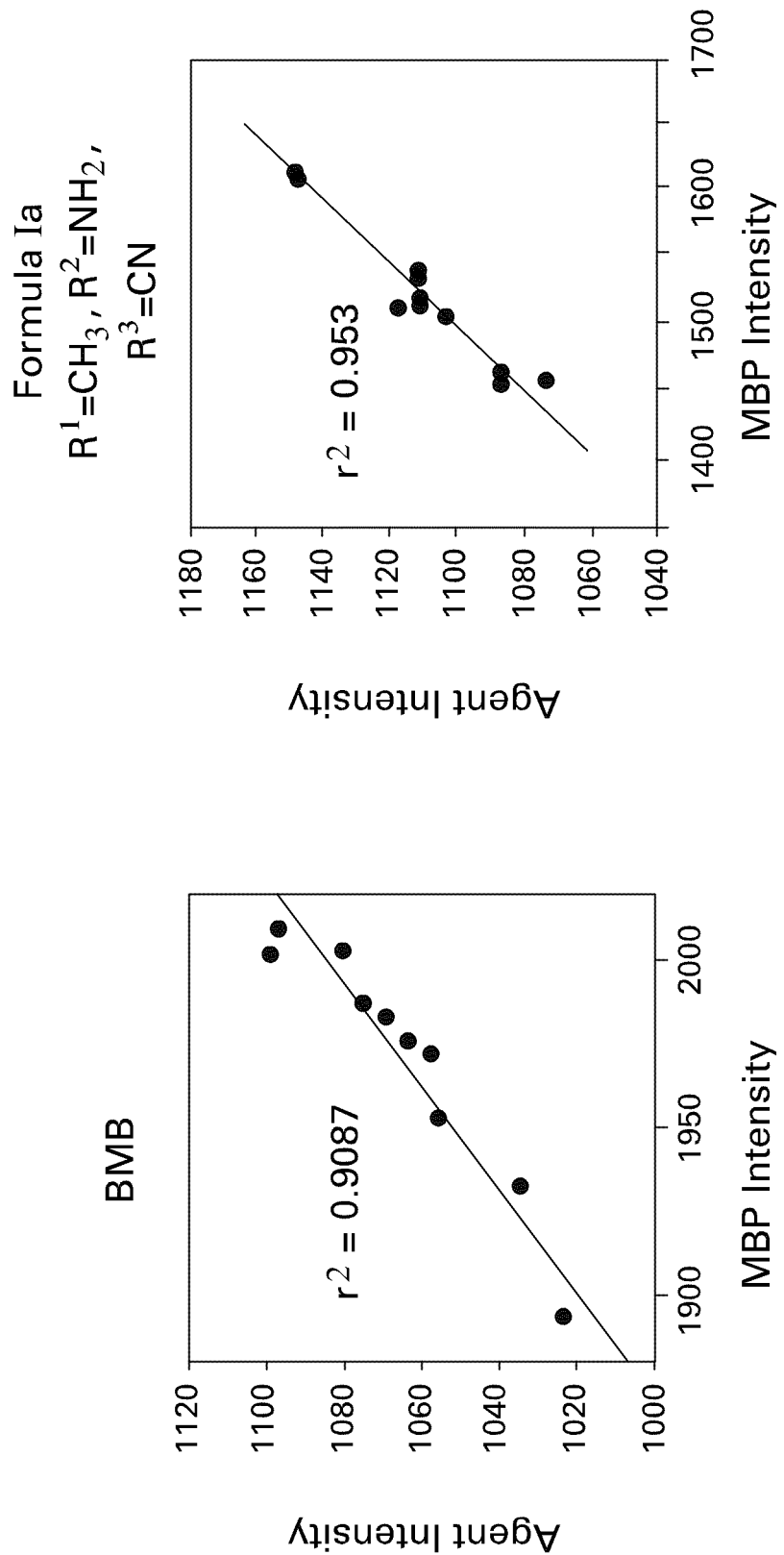
FIG. 4 shows the correlation between the location of MBP signal to that of the fluorophores BMB and Formula Ia ($R1=CH_3$, $R^2=NH_2$ and $R^3=CN$) on the trigeminal nerves of a mouse. BMB or Formula Ia ($R1=CH_3$, $R^2=NH_2$ and $R^3=CN$) were administered to living mice, after adequate time for clearance and biodistrbution, the nerves were resected, sectioned, then stained with MBP antibody.

In some cases, the nerves were resected following in vivo fluorescent imaging. The nerves were sectioned for immunohistochemical analysis. FIG. 4 shows the correlation between the location of MBP signal to that of the fluorophores BMB and Formula Ia ($R^1=CH_3$, $R^2=NH_2$ and $R^3=CN$) on the trigeminal nerves of a mouse. BMB or Formula Ia ($R^1=CH_3$, $R^2=NH_2$ and $R^3=CN$) were administered to living mice, after adequate time for clearance and biodistrbution, the nerves were resected, sectioned, then stained with MBP antibody. FIG. 4 shows a strong co-localization between the fluorophore, administered systemically to the animal, and the MBP antibody, which was administered ex vivo on nerve sections. For Formula Ia ($R^1=CH_3$, $R^2=NH_2$ and $R^3=CN$) the correlation coefficient between the fluorophore staining and the MBP antibody staining was 0.953, providing strong support that the agent are targeting myelin basic protein.

Figure 5:
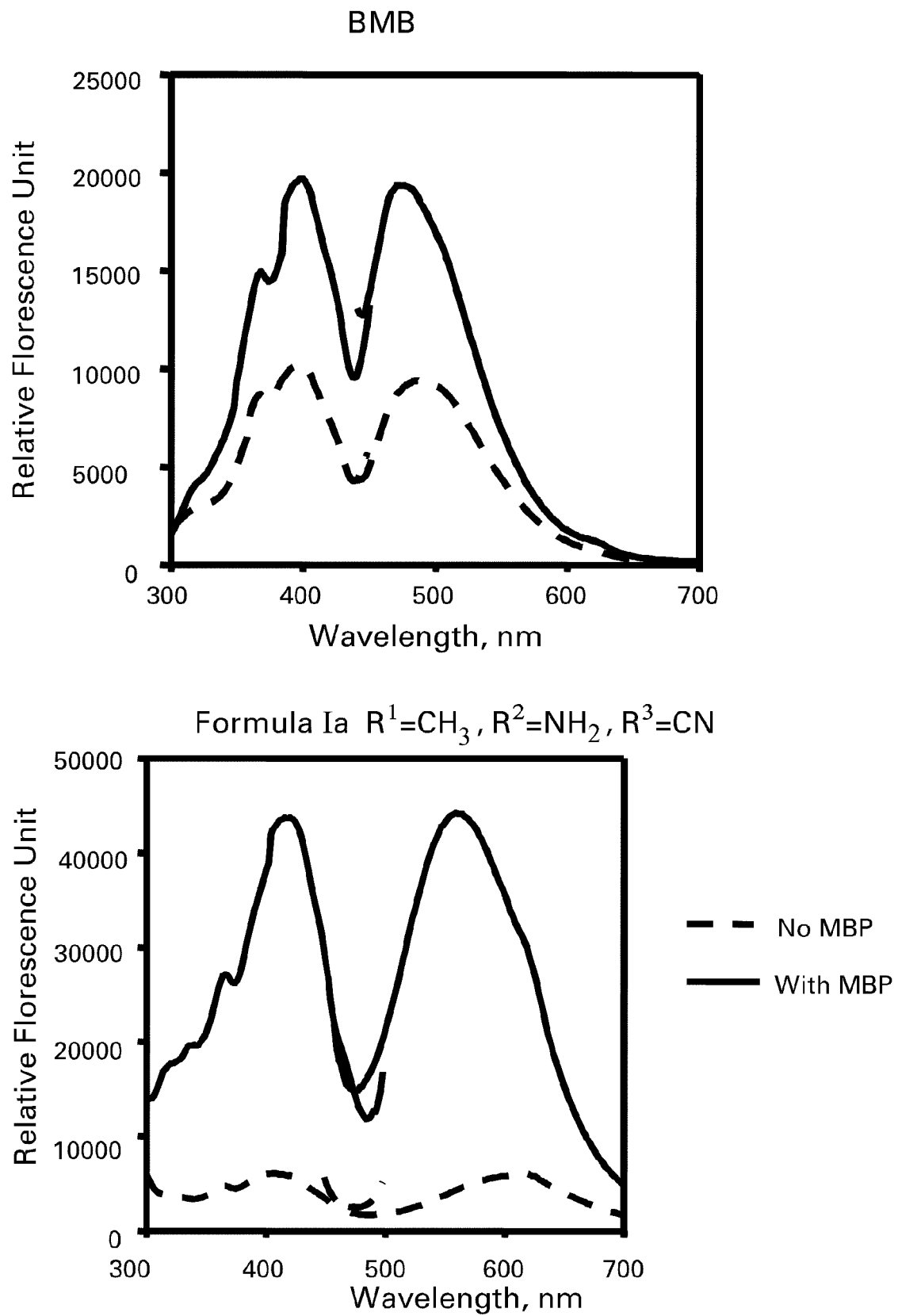
FIG. 5 shows a Spectramax M5 assay on BMB and Formula Ia ($R1=CH_3$, $R^2=NH_2$ and $R^3=CN$) in the presence and absence of purified native-like MBP.

Native myelin basic protein was purified from rat brain and used in biochemical assays. Native MBP altered the fluorescence properties of BMB and Formula Ia wherein $R^1=CH_3$, $R^2=NH_2$ and $R^3=CN$ suggesting a close interaction between the fluorophore and MBP. FIG. 5 shows that the excitation and emission properties of both BMB and Formula Ia ($R^1=CH_3$, $R^2=NH_2$ and $R^3=CN$) were enhanced upon binding to native MBP. The enhancement was much more significant in Formula Ia ($R^1=CH_3$, $R^2=NH_2$ and $R^3=CN$) than in BMB. The conjugation through the π double bond orbitals of the benzene rings and olefinic substituents may provide a path for electrons to flow from the electron-donating group $R^2$ to the electron-donating group $R^3$ across Formula I. This electron flow may contribute to a more pronounced enhancement of the fluorescent signal.

Figure 6:
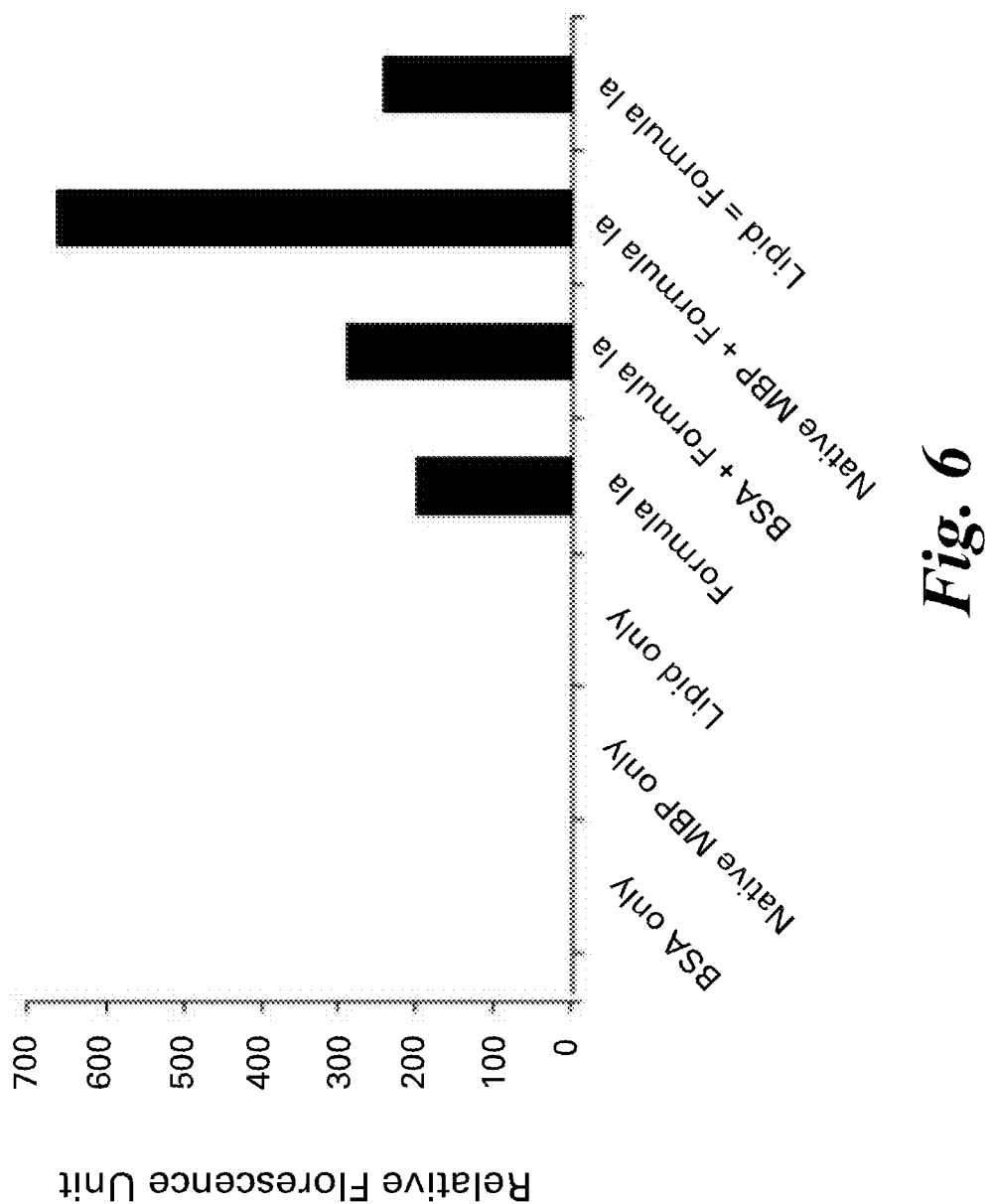
FIG. 6 shows data from a Spectramax M5 assay on Formula Ia ($R1=CH_3$, $R^2=NH_2$ and $R^3=CN$) in the presence of purified native MBP, bovine serum albumin (BSA), or the lipid fraction of native MBP.

To rule out the possibility that the fluorophores were interacting with lipids associated with native MBP, lipids were extracted from native MBP following the Bligh-Dyer method using a chloroform:methanol extraction (*Biochimie*, 1977, 59, 487-96). The extracted lipids were then used in a biochemical assay with a Spectramax M5 microplate reader to determine if a similar enhancement in fluorescence properties of Formula Ia ($R^1=CH_3$, $R^2=NH_2$ and $R^3=CN$) will be observed. FIG. 6 shows that the fluorescence emission of Formula Ia ($R^1=CH_3$, $R^2=NH_2$ and $R^3=CN$) was enhanced only in the presence of native MBP, and not in the presence of extracted lipids or BSA (bovine serum albumin). The results suggest the agents specifically bind to the myelin basic protein component and not to the lipid component.

The invention may be embodied in other specific forms without departing from the spirit or essential characteristics thereof. The foregoing embodiments are therefore to be considered in all respects as illustrative rather than limiting on the invention described herein. The scope of the invention is thus indicated by the appended claims rather than by the foregoing description, and all changes that come within the meaning and range of equivalency of the claims are therefore intended to be embraced therein.

The invention claimed is:

1. A method of detecting myelin-associated neuropathy comprising:
    identifying a subject at risk of or diagnosed with a myelin-associated neuropathy;
    administering to the subject an agent that binds specifically to myelin basic protein wherein said agent comprises;
    a compound of Formula I, a $^{13}C$ enriched compound of Formula I, an $^{19}F$-labeled derivative of Formula I, or a radioisotope derivative of Formula I;

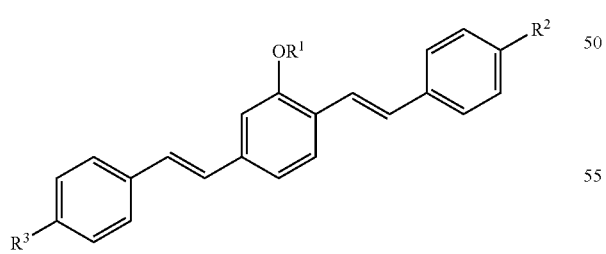

I wherein $R^1$ is an alkyl group;
    $R^2$ is an electron donating group and $R^3$ is an electron withdrawing group; or
    $R^2$ is an electron withdrawing group and $R^3$ is an electron donating group; and
    determining myelination in the subject by detecting the agent present in the subject; and wherein said agent has a large Stokes shift, as measured by at least a 100 nm shift in peak emission of the agent compared to peak excitation of the agent in DMSO; and
    comparing the myelination in the subject with a control sample wherein a lower level of agent in the subject is indicative of a myelin-associated neuropathy.

2. The method of claim 1 wherein $R^1$ is a lower alkyl group of from 1 to 6 carbon atoms.

3. The method of claim 1 wherein the electron donating group is a primary amine, secondary amine, tertiary amine, or alkoxy.

4. The method of claim 1 wherein the electron withdrawing group is a nitrile group or an ester.

5. The method of claim 1 wherein the administering comprises intravenous injection, intraperitoneal injection, subcutaneous injection, intramuscular injection, intrathecal injection, intracerebral injection, intracerebroventricular injection, intraspinal injection, or combinations thereof.

6. The method of claim 1 wherein the detecting is effected by gamma imaging.

7. The method of claim 1 wherein the detecting is effected by MRI, MRS, CEST, PARACEST, or a combination thereof.

8. The method of claim 1 wherein the detecting is effected by:
    applying a light source, tuned to the spectral excitation characteristics of the compound of Formula I; and
    observing the subject through an optical filter tuned to the spectral emission characteristics of the compound of Formula I.

9. The method of claim 1 further comprising the step of quantifying the amount of the agent in the subject.

10. The method of claim 9 wherein the quantifying step comprises measuring radioactivity of the agent.

11. The method of claim 1 wherein the myelin-associated neuropathy comprises multiple sclerosis, Guillain-Barré syndrome, leukodystrophies metachromatic leukodystrophy, Refsum's disease, adrenoleukodystrophy, Krabbe's disease, phenylketonuria, Canavan disease, Pelizaeus-Merzbacher disease, Alexander's disease, diabetic neuropathy, chemotherapy-induced neuropathy, or a combination thereof.

12. A method of imaging myelin basic protein in a surgical field comprising the steps of:
    contacting the surgical site with an agent that binds specifically to myelin basic protein and wherein the agent comprises;
    a compound of Formula I, a $^{13}C$ enriched compound of Formula I, an $^{19}F$-labeled derivative of Formula I, or a radioisotope derivative of Formula I

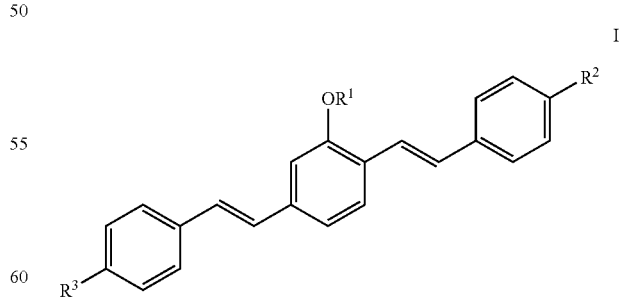

I wherein $R^1$ is an alkyl group;
    $R^2$ is an electron donating group and $R^3$ is an electron withdrawing group; or
    $R^2$ is an electron withdrawing group and $R^3$ is an electron donating group; and detecting the agent; and wherein said agent has a large Stokes shift, as measured by at least a 100 nm shift in peak emission of the agent compared to peak excitation of the agent in DMSO.

13. The method of claim 12 wherein $R^1$ is a lower alkyl group of from 1 to 6 carbon atoms.

14. The method of claim 12 wherein the electron donating group is a primary amine, secondary amine, tertiary amine, or alkoxy.

15. The method of claim 12 wherein the electron withdrawing group is a nitrile group or an ester.

16. The method of claim 12 wherein the surgical site is an open surgical field or a minimally invasive field.

17. The method of claim 12 wherein the contacting step comprises direct application of the agent to a surgical site.

18. The method of claim 17 wherein the agent is dissolved or suspended in a pharmaceutical carrier suitable for surgical irrigation.

19. The method of claim 12 wherein the contacting step comprises a parenteral administration of the agent.

20. The method of claim 19 wherein the parenteral administration comprises subcutaneous injection, intraperitoneal injection, intramuscular injection, intravenous injection, intrathecal injection, intracerebroventricular injection, intraspinal injection, or any combination thereof.

21. The method of claim 12 wherein the detecting step comprises:
applying a light source, tuned to the spectral excitation characteristics of the agent, to the surgical field; and
observing the surgical field through an optical filter tuned to the spectral emission characteristics of the agent.

22. The method of claim 12 wherein the detecting step involves gamma imaging of the surgical site.

23. A method of quantifying the amount of myelin present in a tissue sample comprising:
contacting the tissue sample with an agent that binds specifically to myelin basic protein wherein the agent comprises;
a compound of Formula I, a $^{13}C$ enriched compound of Formula I, an $^{19}F$-labeled derivative of Formula I, or a radioisotope derivative of Formula I;

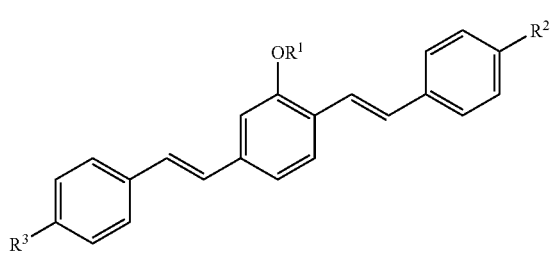

wherein $R^1$ is an alkyl group;
$R^2$ is an electron donating group and $R^3$ is an electron withdrawing group; or
$R^2$ is an electron withdrawing group and $R^3$ is an electron donating group;
detecting myelinated tissue in the tissue sample by detecting the agent present in the tissue sample wherein said agent has a large Stokes shift, as measured by at least a 100 nm shift in peak emission of the agent compared to peak excitation of the agent in DMSO; and
quantifying the amount of the agent present in the tissue sample by comparing to a baseline measurement of myelin basic protein in a control sample.

24. The method of claim 23 wherein $R^1$ is a lower alkyl group of from 1 to 6 carbon atoms.

25. The method of claim 23 wherein the electron donating group is a primary amine, secondary amine, tertiary amine, or alkoxy group.

26. The method of claim 23 wherein the electron withdrawing group is a nitrile group or an ester.

27. The method of claim 23 wherein the detecting is effected by fluorescence microscopy, laser-confocal microscopy, cross-polarization microscopy, autoradiography, magnetic resonance imaging, magnetic resonance spectroscopy, or a combination thereof.

28. A kit for detecting myelin-associated neuropathy in a subject comprising:
an agent that binds specifically to myelin basic protein wherein the agent comprises a compound of Formula I, a $^{13}C$ enriched compound of Formula I, an $^{19}F$-labeled derivative of Formula I, or a radioisotope derivative of Formula I

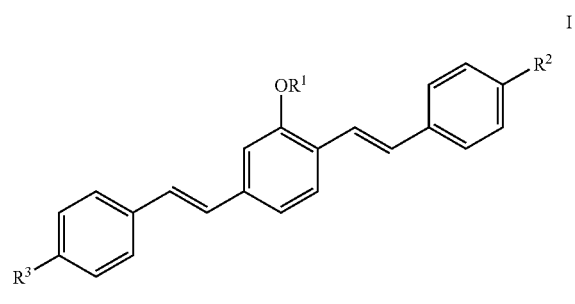

wherein $R^1$ is an alkyl group;
$R^2$ is an electron donating group and $R^3$ is an electron withdrawing group; or
$R^2$ is an electron withdrawing group and $R^3$ is an electron donating group; and
wherein said agent has a large Stokes shift, as measured by at least a 100 nm shift in peak emission of the agent compared to peak excitation of the agent in DMSO; and
a pharmaceutical carrier.

* * * * *